(12) United States Patent
Hitchcock et al.

(10) Patent No.: US 9,670,229 B2
(45) Date of Patent: Jun. 6, 2017

(54) 5-HT3 RECEPTOR ANTAGONISTS

(71) Applicant: Takeda Pharmaceutical Company Limited, San Diego, CA (US)

(72) Inventors: Stephen Hitchcock, San Diego, CA (US); Holger Monenschein, San Diego, CA (US); Holly Reichard, San Diego, CA (US); Huikai Sun, San Diego, CA (US); Shota Kikuchi, San Diego, CA (US); Todd Macklin, San Diego, CA (US); Maria Hopkins, San Diego, CA (US)

(73) Assignee: Takeda Pharmaceutical Company Limited, Osaka (JP)

(*) Notice: Subject to any disclaimer, the term of this patent is extended or adjusted under 35 U.S.C. 154(b) by 0 days.

(21) Appl. No.: 15/150,013

(22) Filed: May 9, 2016

(65) Prior Publication Data

US 2016/0251373 A1    Sep. 1, 2016

Related U.S. Application Data

(62) Division of application No. 14/645,639, filed on Mar. 12, 2015, now Pat. No. 9,346,829, which is a division of application No. 13/943,634, filed on Jul. 16, 2013, now Pat. No. 9,012,447.

(60) Provisional application No. 61/708,521, filed on Oct. 1, 2012, provisional application No. 61/672,709, filed on Jul. 17, 2012.

(51) Int. Cl.
| | |
|---|---|
| *C07D 519/00* | (2006.01) |
| *C07D 498/08* | (2006.01) |
| *C07D 471/04* | (2006.01) |
| *C07D 451/12* | (2006.01) |
| *C07D 221/22* | (2006.01) |
| *A61K 31/19* | (2006.01) |
| *A61K 31/5386* | (2006.01) |
| *C07C 53/40* | (2006.01) |
| *C07D 453/02* | (2006.01) |
| *C07D 471/08* | (2006.01) |
| *C07C 53/18* | (2006.01) |

(52) U.S. Cl.
CPC ............ *C07D 498/08* (2013.01); *A61K 31/19* (2013.01); *A61K 31/5386* (2013.01); *C07C 53/18* (2013.01); *C07C 53/40* (2013.01); *C07D 221/22* (2013.01); *C07D 451/12* (2013.01); *C07D 453/02* (2013.01); *C07D 471/04* (2013.01); *C07D 471/08* (2013.01); *C07D 519/00* (2013.01)

(58) Field of Classification Search
CPC .. C07D 519/00; C07D 498/08; C07D 471/04; C07D 451/12; C07D 221/22; A61K 31/19; A61K 31/5386

USPC ................ 514/230.5, 299; 544/105; 546/121
See application file for complete search history.

(56) References Cited

U.S. PATENT DOCUMENTS

| | | | |
|---|---|---|---|
| 4,789,673 A | 12/1988 | Donatsch et al. | |
| 4,803,199 A | 2/1989 | Donatsch et al. | |
| 4,886,808 A | 12/1989 | King et al. | |
| 4,910,193 A | 3/1990 | Buchheit et al. | |
| 5,034,398 A | 7/1991 | King et al. | |
| 5,298,510 A | 3/1994 | Tyers | |
| 5,344,831 A | 9/1994 | Satoh et al. | |
| 9,012,447 B2 * | 4/2015 | Hitchcock ............ | C07D 498/08 514/230.5 |
| 9,346,829 B2 * | 5/2016 | Hitchcock ............ | C07D 498/08 |
| 2004/0038958 A1 | 2/2004 | Rundfeldt et al. | |
| 2005/0234095 A1 | 10/2005 | Xie et al. | |
| 2007/0191313 A1 | 8/2007 | Beard et al. | |

(Continued)

FOREIGN PATENT DOCUMENTS

| | | |
|---|---|---|
| EP | 0200444 | 5/1986 |
| EP | 0469449 | 2/1992 |
| EP | 0491664 | 6/1992 |

(Continued)

OTHER PUBLICATIONS

Naghdi et al. "The effect of intrahippocampal injections of ritanserin (5HT2A/2C antagonist) and granisetron (5HT3 antagonist) on learning as assessed in the spatial version of the water maze" Behavioural Brain Research 157 (2005) p. 205-210.

(Continued)

*Primary Examiner* — Kahsay Habte
(74) *Attorney, Agent, or Firm* — Matthew J. Russo; David M. Stemerick

(57) ABSTRACT

The present invention provides 5-HT3 receptor antagonists of Formula (I):

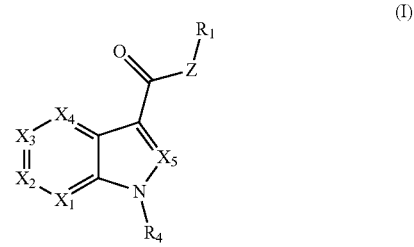

which are useful for the treatment of diseases treatable by inhibition of 5-HT3 receptor such as emesis, pain, drug addiction, neurodegenerative and psychiatric disorders, and GI disorders. Also provided are pharmaceutical compositions containing such compounds and processes for preparing such compounds.

11 Claims, No Drawings

(56) References Cited

U.S. PATENT DOCUMENTS

2011/0319407 A1  12/2011  Xie et al.

FOREIGN PATENT DOCUMENTS

| | | |
|---|---|---|
| EP | 0558923 | 9/1993 |
| EP | 0708105 | 4/1996 |
| EP | 1156045 | 11/2001 |
| EP | 1243268 | 9/2002 |
| WO | WO/95/27490 | 10/1995 |
| WO | WO/03/035625 | 5/2003 |
| WO | WO/2004/006920 | 1/2004 |
| WO | WO/2004/029050 | 4/2004 |
| WO | WO/2005/092890 | 10/2005 |
| WO | WO/2006/077365 | 7/2006 |
| WO | WO/2007/038367 | 4/2007 |
| WO | WO/2007/095561 | 8/2007 |
| WO | WO/2008/048981 | 4/2008 |
| WO | WO/2008/097930 | 8/2008 |
| WO | WO/2008/100867 | 8/2008 |
| WO | WO/2009/023623 | 2/2009 |
| WO | WO/2011/126821 | 10/2011 |
| WO | WO/2011/153553 | 12/2011 |

OTHER PUBLICATIONS

Javadi-Paydar et al. "Involvement of nitric oxide in granisetron improving effect on scopolamine-induced memory impairment in mice" Brain Research 1 4 2 9 (2 0 1 2) p. 6 1-7 1.

* cited by examiner

5-HT3 RECEPTOR ANTAGONISTS

RELATED APPLICATIONS

This application claims the benefit of U.S. Provisional Application No. 61/672,709, filed Jul. 17, 2012, and U.S. Provisional Application No. 61/708,521, filed Oct. 1, 2012, which are herein incorporated by reference.

FIELD OF INVENTION

The present invention provides compounds that are 5-HT3 receptor antagonists and are therefore useful for the treatment of diseases treatable by inhibition of the 5-HT3 receptor such as emesis, pain, drug addiction, neurodegenerative and psychiatric disorders, and GI disorders. Also provided are pharmaceutical compositions containing such compounds and processes for preparing such compounds.

BACKGROUND

Serotonin type 3 (5-HT3) receptors are part of the serotonergic system. Unlike other receptors of this system, which are all G-protein coupled receptors, the 5-HT3 receptors are ligand-gated ion channels and belongs to the superfamily of Cys-loop receptors that include nicotinic acetylcholine, γ-aminobutyric acid (GABA)A and glycine receptors and a Zn+2 activated cation channel (see Davies et al., 2003, *J. Biol. Chem.*, 278, 712-717; Connolly et al., 2004, *Biochem Soc Trans* 32, 529-534). The 5-HT$_3$ receptors are made up of 5 subunits arranged around a central ion conducting pore, which is permeable to sodium, potassium, and calcium ions (see Boess et al., 1995, *J. Neurochem.* 64, 1401-1405; Connolly et al., 2004, *Biochem Soc Trans* 32, 529-534). Binding of serotonin to the 5-HT$_3$ receptors opens the channel, which, in turn, leads to an excitatory response in neurons. Functional data reported for 5-HT3 receptors refer to 5-HT3A or 5-HT3AB receptors since the properties of these receptor subtypes have been most extensively studies to date.

5-HT3 receptors are known to be expressed in the central nervous system in regions involving vomiting reflex, processing of pain, cognition and anxiety control and play a role in the pathogenesis of diseases such as emesis, migraine, drug addiction, and neurodegenerative and psychiatric disorders such as anxiety and depression (see Hewlett et al., 2003 *J. Clin. Psychiatry* 64, 1025-1030; Kelley et al., 2003a, *Eur J Pharmacol.*, 461, 19-25; Haus et al., 2000 *Scand J Rheumatol Suppl* 113, 55-58; and Faris et al., 2006 *J affect Disorder* 92, 79-90), eating disorders (Hammer et al., 1990 *Am J Physiol* 259, R627-R636, and Jiang & Gietzen 1994 *Pharmacol Biochem Behav* 47, 59-63), schizophrenia (see Hermann et al. 1996 *Biochem Biophys Res Commun* 225, 957-960; Sirota et al., 2000 *Am J Psychiatry* 157, 287-289; Adler et al., 2005 *Am J Psychiatry* 162, 386-388; Koike et al., Levkovitz et al, 2005 *Schizophr Res* 76, 67-72), cognitive dysfunction associated with schizophrenia (see Zhang et al., 2006 *Schizophr Res* 88, 102-110; Akhondzadeh et al., 2009 *Schizophr Res* 107, 206-212), congnitive dysfuntion associated with Parkinson's disease, Huntington's Chorea, presenile dementias and Alzheimer's disease (see Costall and Naylor 2004 *CNS Neurol Disord* 3, 27-37) substance abuse and addiction (see Johnson et al., 2002 *Psychopharmacology* (Berl) 160, 408-413; Johnson, 2004 *CNS Drugs* 18, 1105-1118; Dawes et al., 2005 *Addict Behav* 30, 1630-1637, Johnson 2006 *Drug Alcohol Depend* 84, 256-263), autish spectrum disorders (see Anderson et al *Neurogenetics* 10, 209-216) and pain (see Kayser et al, 2007 *Pain* 130, 235; Glaum et al., 1998 *Neurosci Lett* 95, 313-317; Schworer & Ramadori 1993 *Clin Investig* 71, 659; Thompson and Lummis 2007 *Exp Opin Ther Targets*, 11, 527-540). In addition, 5-HT3 receptors are expressed in the GI tract and hence may play a role in GI disorders such as dyspepsia, gastroesophagal reflux disease and irritable bowel syndrome (see Graeff 1997 *Psychiatr Clin North Am* 20, 723; Thompson and Lummis 2007 *Exp Opin Ther Targets*, 11, 527-540; Barnes et al. 2009 *Neuropharmacology* 56, 273). Expression of the 5-HT3A subunit has also been discovered extraneuronally in immune cells such as monocyes, chondrocytes, T-cells, synovial tissue and platelets (Fiebich et al., 2004 *Scan J Rheumatol Suppl*, 9-11, Stratz et al., 2008 *Thromb Haemost* 99, 784) and of 5-HT3A, C-E within the lamina propia in the epithelium of the gut mucose (Kapeller et al., J Comp Neuro., 2008; 509: 356-371) thus suggesting they may be involved in immunological and inflammatory diseases like atherosclerosis, tendomyopathies and fibromyalgia.

The 5-HT3 antagonists currently on the market are approved only for the treatment of emesis or irritable bowel syndrome. It is desirable to discover 5-HT3 antagonists that can be used to treat other diseases amenable to alleviation by 5-HT3 receptors such as schizophrenia and cognitive disorder associated with schizophrenia. The present invention can fulfill this and related needs. It is desirable to discover 5-HT3 antagonists that have desirable pharmacokinetic and pharmacodynamic properties, such as selectivity over nicotinic-α7 receptors.

Certain antagonists the 5-HT3 receptor are described in U.S. Pat. Nos. 4,789,763; 4,803,199; 4,886,808; 4,910,193; 5,334,831; EP 0 469 449; and EP 0 491 664. Certain inhibitors of TGF-β are described in EP 1 156 045 and certain treatment of nephritis is described in EP1 243 268. Certain antagonists of 5-HT4 are described in EP 0 708 105. Certain ligands of nicotinic-α7 receptors are described in WO 2007/038367. Certain P2X7 antagonists are disclosed in WO 2009/023623.

SUMMARY

In a first aspect, this invention is directed to a compound of Formula (I):

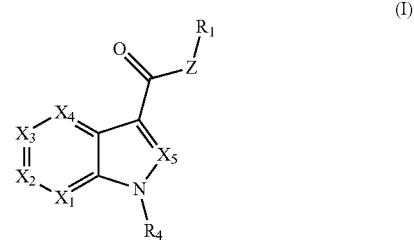

(I)

wherein:
Z is O or NR$_a$ where R$_a$ is hydrogen or C$_{1-6}$ alkyl;
R$_1$ is a ring of the formula (a)-(h) below:

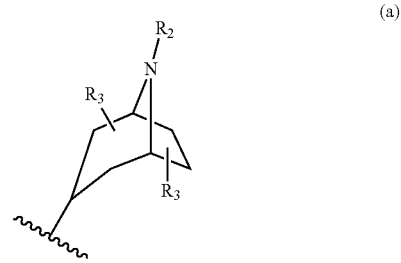

(a)

-continued

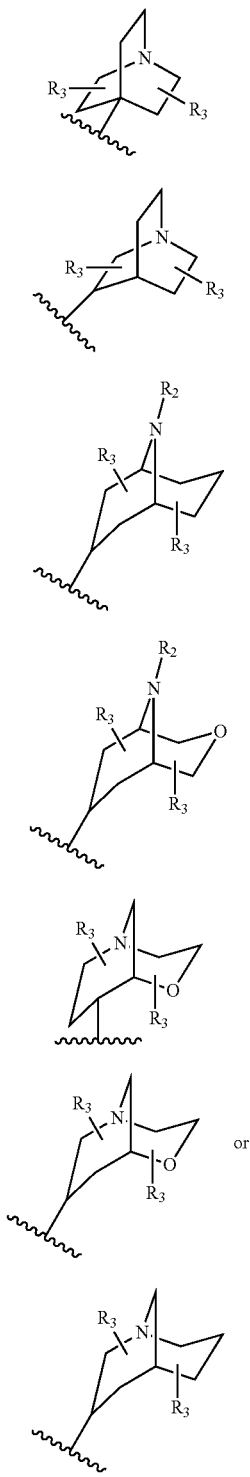

$R_2$ is hydrogen, $C_{1-6}$ alkyl, or $C_{1-6}$ haloalkyl;
each $R_3$ is independently hydrogen, $C_{1-6}$ alkyl, $C_{1-6}$ alkoxy, $C_{1-6}$ haloalkoxy, or halo and can be present on any carbon atom in the rings;
$R_4$ is pyridinyl or pyrazolyl each optionally substituted with one or two substituents independently selected from $C_{1-6}$ alkyl, $C_{1-6}$ haloalkyl, $C_{1-6}$ haloalkoxy, $C_{1-6}$ alkoxy, cyano, or halo;

all of $X_1$-$X_4$ are $CR_5$ or one of $X_1$-$X_4$ is N and the others are $CR_5$;
each $R_5$ is independently hydrogen, $C_{1-6}$ alkyl, halo, hydroxy, or cyano provided that at least one of $R_5$ is hydrogen;
$X^5$ is N or $CR^6$ where $R^6$ is hydrogen, $C_{1-6}$ alkyl, or halo;
or a pharmaceutically acceptable salt thereof or N-oxide thereof.

In a second aspect, this present invention is directed to a pharmaceutical composition comprising a compound of Formula (I) (or any embodiments thereof disclosed herein) or a pharmaceutically acceptable salt thereof and a pharmaceutically acceptable excipient.

In a third aspect, this present invention is directed to a method of treating a disease treatable by administration of a 5-HT3 receptor antagonist which method comprises administrating to the patient a pharmaceutical composition comprising a compound of Formula (I) (or any embodiments thereof disclosed herein) and/or a pharmaceutically acceptable salt and a pharmaceutically acceptable excipient. That is, the present invention provides a method of treating a disease treatable by administration of a 5-HT3 receptor antagonist comprising: administrating to a patient in need thereof a therapeutically effective amount of a compound of Formula (I) (or any embodiments thereof disclosed herein) or a pharmaceutically acceptable salt thereof.

In one embodiment of the third aspect, the disease treatable by administration of a 5-HT3 receptor antagonist is emesis, migraine, substance abuse and addiction, neurodegenerative and psychiatric disorders such as anxiety and depression, eating disorders, schizophrenia, cognitive dysfunction associated with schizophrenia, Parkinson's disease, Huntington's Chorea, presenile dementias and Alzheimer's disease, and pain; GI disorders such as dyspepsia, gastroesophagal reflux disease, and irritable bowel syndrome; and immunological disorders and inflammation such as atherosclerosis, tendomyopathies and fibromyalgia. In another embodiment of the third aspect the disease treatable by administration of a 5-HT3 receptor antagonist is schizophrenia or cognitive dysfunction associated with schizophrenia.

In a fourth aspect, the compound of Formula (I) (or any embodiments thereof disclosed herein) or a pharmaceutically acceptable salt thereof is administered in combination with an antipsychotic drug. In one embodiment of the fourth aspect, the antipsychotic drug is AMG 747, bitopertin (RG1678), RG1578, AMG579, GSK1018921, aripiprazole, risperidone, olanzapine, quetiapine, ziprasidone, or clozapine.

In a fifth aspect, the invention is directed to use of compound of Formula (I) (or any embodiments thereof disclosed herein) or a pharmaceutically acceptable salt thereof as a medicament.

In a sixth aspect, the invention is directed to a compound of Formula (I) (or any embodiments thereof disclosed herein) or a pharmaceutically acceptable salt thereof for use to treat a disease treatable by administration of a 5-HT3 receptor antagonist as disclosed herein.

In one embodiment of the fifth and sixth aspects, the use is for the treatment of emesis, migraine, substance abuse and addiction, neurodegenerative and psychiatric disorders such as anxiety and depression, eating disorders, schizophrenia, cognitive dysfunction associated with schizophrenia, Parkinson's disease, Huntington's Chorea, presenile dementias and Alzheimer's disease, and pain; GI disorders such as dyspepsia, gastroesophagal reflux disease, and irritable bowel syndrome; and immunological disorders and inflammation such as atherosclerosis, tendomyopathies and fibromyalgia. In another embodiment of the fifth and the sixth aspects the use is for the treatment of schizophrenia or cognitive dysfunction associated with schizophrenia also known as cognitive impairment associated with schizophrenia. In yet another embodiment of the fifth and the sixth aspects, and embodiments contained therein, the compound of Formula (I) is administered in combination with an antipsychotic drug. In one embodiment, the antipsychotic drug is AMG 747, bitopertin (RG1678), RG1578, AMG579, GSK1018921, aripiprazole, risperidone, olanzapine, olanzapine quetiapine, or ziprasidone, clozapine.

DETAILED DESCRIPTION OF THE INVENTION

Definitions:

Unless otherwise stated, the following terms used in the specification and claims are defined for the purposes of this Application and have the following meaning:

"$C_{1-6}$ alkyl" means a linear saturated monovalent hydrocarbon radical of one to six carbon atoms or a branched saturated monovalent hydrocarbon radical of three to six carbon atoms, e.g., methyl, ethyl, propyl, 2-propyl, butyl (including all isomeric forms), pentyl (including all isomeric forms), and the like.

"$C_{1-6}$ alkoxy" means a —OR radical where R is $C_{1-6}$ alkyl as defined above, e.g., methoxy, ethoxy, propoxy, or 2-propoxy, n-, iso-, or tert-butoxy, and the like.

"$C_{1-6}$ haloalkyl" means $C_{1-6}$ alkyl radical as defined above, which is substituted with one or more halogen atoms, preferably one to five halogen atoms, preferably fluorine or chlorine, including those substituted with different halogens, e.g., —$CH_2Cl$, —$CF_3$, —$CHF_2$, —$CH_2CF_3$, —$CF_2CF_3$, —$CF(CH_3)_2$, and the like. When the $C_{1-6}$ alkyl is substituted with only fluoro, it can be referred to in this Application as $C_{1-6}$ fluoroalkyl.

"$C_{1-6}$ haloalkoxy" means a —OR radical where R is $C_{1-6}$ haloalkyl as defined above e.g., —$OCF_3$, —$OCHF_2$, and the like. When R is haloalkyl where the $C_{1-6}$ alkyl is substituted with only fluoro, it can be referred to in this Application as $C_{1-6}$ fluoroalkoxy.

"Halo" means fluoro, chloro, bromo, or iodo, preferably fluoro or chloro.

The present invention also includes the prodrugs of compounds of Formula (I). The term prodrug is intended to represent covalently bonded carriers, which are capable of releasing the active ingredient of Formula (I) respectively, when the prodrug is administered to a mammalian subject. Release of the active ingredient occurs in vivo. Prodrugs can be prepared by techniques known to one skilled in the art. These techniques generally modify appropriate functional groups in a given compound. These modified functional groups however regenerate original functional groups in vivo or by routine manipulation. Prodrugs of compounds of Formula (I) include compounds wherein a hydroxy, amino, carboxylic, or a similar group is modified. Examples of prodrugs include, but are not limited to esters (e.g., acetate, formate, and benzoate derivatives), carbamates (e.g., N,N-dimethylaminocarbonyl) of hydroxy or amino functional groups in compounds of Formula (I)), amides (e.g., trifluoroacetylamino, acetylamino, and the like), and the like. Prodrugs of compounds of Formula (I) are also within the scope of this invention.

The present invention also includes protected derivatives of compounds of Formula (I). For example, when compounds of Formula (I) contain groups such as hydroxy, carboxy, thiol or any group containing a nitrogen atom(s), these groups can be protected with a suitable protecting groups. A comprehensive list of suitable protective groups can be found in T. W. Greene, *Protective Groups in Organic Synthesis*, John Wiley & Sons, Inc. (1999), the disclosure of which is incorporated herein by reference in its entirety. The protected derivatives of compounds of Formula (I) can be prepared by methods well known in the art.

A "pharmaceutically acceptable salt" of a compound means a salt that is pharmaceutically acceptable and that possesses the desired pharmacological activity of the parent compound. Such salts include: acid addition salts, formed with inorganic acids such as hydrochloric acid, hydrobromic acid, sulfuric acid, nitric acid, phosphoric acid, and the like; or formed with organic acids such as formic acid, acetic acid, propionic acid, hexanoic acid, cyclopentanepropionic acid, glycolic acid, pyruvic acid, lactic acid, malonic acid, succinic acid, malic acid, maleic acid, fumaric acid, tartaric acid, citric acid, benzoic acid, 3-(4-hydroxybenzoyl)benzoic acid, cinnamic acid, mandelic acid, methanesulfonic acid, ethanesulfonic acid, 1,2-ethanedisulfonic acid, 2-hydroxyethanesulfonic acid, benzenesulfonic acid, 4-chlorobenzenesulfonic acid, 2-naphthalenesulfonic acid, 4-toluenesulfonic acid, camphorsulfonic acid, glucoheptonic acid, 4,4'-methylenebis-(3-hydroxy-2-ene-1-carboxylic acid), 3-phenylpropionic acid, trimethylacetic acid, tertiary butylacetic acid, lauryl sulfuric acid, gluconic acid, glutamic acid, hydroxynaphthoic acid, salicylic acid, stearic acid, muconic acid, and the like; or salts formed when an acidic proton present in the parent compound either is replaced by a metal ion, e.g., an alkali metal ion, an alkaline earth ion, or an aluminum ion; or coordinates with an organic base such as ethanolamine, diethanolamine, triethanolamine, tromethamine, N-methylglucamine, and the like. It is understood that the pharmaceutically acceptable salts are non-toxic. Additional information on suitable pharmaceutically acceptable salts can be found in *Remington's Pharmaceutical Sciences*, 17th ed., Mack Publishing Company, Easton, Pa., 1985, which is incorporated herein by reference.

The compounds of the present invention may have asymmetric centers. Compounds of the present invention containing an asymmetrically substituted atom may be isolated in optically active or racemic forms. It is well known in the art how to prepare optically active forms, such as by resolution of materials. All chiral, diastereomeric, meso, racemic forms are within the scope of this invention, unless the specific stereochemistry or isomeric form is specifically indicated.

Additionally, as used herein the term $C_{1-6}$ alkyl and terms derived therefrom includes all the possible isomeric forms of said $C_{1-6}$ alkyl group. Furthermore, the heteroaryl include all the positional isomers. Furthermore, all polymorphic forms and hydrates of a compound of Formula (I) are within the scope of this invention.

The terms "compound" and "a compound of the invention" and "compound of the present invention" and the like, and their plural forms include the embodiment of Formula (I) and the other more particular embodiments encompassed by Formula (I) described herein and exemplified compounds described herein or a pharmaceutically acceptable salt of each of these embodiments. All references to compounds, include all isotopes of the atoms contained therein, including isotopically-labeled compounds.

The compounds of the present invention exist as tautomers. All tautomeric forms the compounds of the invention are contemplated to be within the scope of the present invention.

"Optional" or "optionally" means that the subsequently described event or circumstance may but need not occur, and that the description includes instances where the event or circumstance occurs and instances in which it does not.

A "pharmaceutically acceptable carrier or excipient" means a carrier or an excipient that is useful in preparing a pharmaceutical composition that is generally safe, non-toxic and neither biologically nor otherwise undesirable, and includes a carrier or an excipient that is acceptable for veterinary use as well as human pharmaceutical use. "A pharmaceutically acceptable carrier/excipient" as used in the specification and claims includes both one and more than one such excipient. Pharmaceutically acceptable excipients are well known in the art, such as those in *Remington's Pharmaceutical Sciences,* 17th ed., Mack Publishing Company, Easton, Pa., 1985.

The terms "condition," "disorder," and "disease" relate to any unhealthy or abnormal state.

"Treat," "treating," or "treatment" of a disease includes:

(1) preventing the disease, i.e. causing the clinical symptoms of the disease not to develop in a mammal that may be exposed to or predisposed to the disease but does not yet experience or display symptoms of the disease;

(2) inhibiting the disease, i.e., arresting, controlling, slowing, stopping, or reducing the development of the disease or its clinical symptoms; or (3) relieving the disease, i.e., causing regression of the disease or its clinical symptoms or improvement of the disease or its clinical symptoms The terms "treat," "treating," and "treatment," do not necessarily indicate a total elimination of any or all symptoms or a cure of the disease.

As used herein the terms "patient" and "subject" includes humans and non-human animals, for example, mammals, such as mice, rats, guinea pigs, dogs, cats, rabbits, cows, horses, sheep, goats, and pigs. The term also includes birds, fish, reptiles, amphibians, and the like. It is understood that a more particular patient is a human. Also, more particular patients and subjects are non-human mammals, such as mice, rats, and dogs.

A "therapeutically effective amount" means the amount of a compound of Formula (I) or a pharmaceutically acceptable salt thereof that, when administered in single or multiple doses, to a mammal for treating a disease, is sufficient to effect such treatment for the disease. The "therapeutically effective amount" will vary depending on the compound, the disease and its severity and the age, weight, etc., of the mammal to be treated, the degree of or involvement or the severity of the condition, disorder, or disease, the response of the individual patient; the particular compound administered; the mode of administration; the bioavailability characteristics of the preparation administered; the dose regimen selected; the use of concomitant medication; and other relevant circumstances.

The term "disease treatable by administration of a 5-HT3 receptor antagonist" includes emesis, migraine, substance abuse and addiction, neurodegenerative and psychiatric disorders such as anxiety and depression, eating disorders, schizophrenia, cognitive dysfunction associated with schizophrenia, Parkinson's disease, Huntington's Chorea, presenile dementias and Alzheimer's disease, and pain; GI disorders such as dyspepsia, gastroesophagal reflux disease, and irritable bowel syndrome; and immunological disorders and inflammation such as atherosclerosis, tendomyopathies and fibromyalgia. In a particular embodiment the disease is cognitive dysfunction associated with schizophrenia also known as cognitive impairment associated with schizophrenia.

Representative compounds of the Invention are shown in Table I below:

| Cpd. No. | (I) 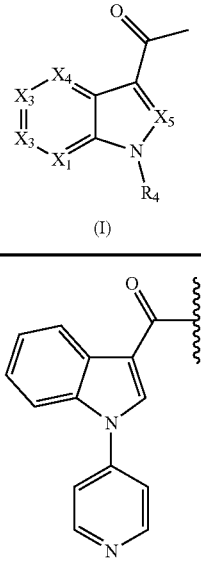 | —Z—R[1] | Salt | Name | MW Calcd. | MS Obs. (M + 1)+ |
|---|---|---|---|---|---|---|
| 1 | 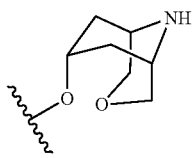 [SMILES: *OC1CC2COCC(C1)N2] | 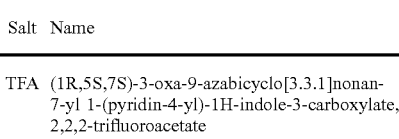 | TFA | (1R,5S,7S)-3-oxa-9-azabicyclo[3.3.1]nonan-7-yl 1-(pyridin-4-yl)-1H-indole-3-carboxylate, 2,2,2-trifluoroacetate | 363.4097 | 364.3 |
| 2 | 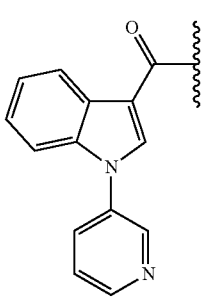 [SMILES: *C(=O)c1cn(-c2cccnc2)c2ccccc12] | 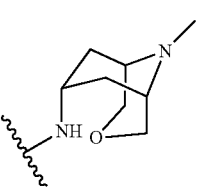 [SMILES: *NC1CC2COCC(C1)N2C] | TFA | N-((1R,5S,7S)-9-methyl-3-oxa-9-azabicyclo[3.3.1]nonan-7-yl)-1-(pyridin-3-yl)-1H-indole-3-carboxamide, 2,2,2-trifluoroacetate | 376.4516 | 377.2 |

-continued

| Cpd. No. | (I) | —Z—R¹ | Salt | Name | MW Calcd. | MS Obs. (M + 1)⁺ |
|---|---|---|---|---|---|---|
| 3 | indol-3-yl with N-(pyridin-2-yl) | 9-methyl-3-oxa-9-azabicyclo[3.3.1]nonan-7-yl-NH- | TFA | N-((1R,5S,7S)-9-methyl-3-oxa-9-azabicyclo[3.3.1]nonan-7-yl)-1-(pyridin-2-yl)-1H-indole-3-carboxamide, 2,2,2-trifluoroacetate | 376.4516 | 377.3 |
| 4 | indol-3-yl with N-(pyridin-4-yl) | 9-methyl-3-oxa-9-azabicyclo[3.3.1]nonan-7-yl-NH- | TFA | N-((1R,5S,7S)-9-methyl-3-oxa-9-azabicyclo[3.3.1]nonan-7-yl)-1-(pyridin-4-yl)-1H-indole-3-carboxamide, 2,2,2-trifluoroacetate | 376.4516 | 377.2 |
| 5 | indol-3-yl with N-(pyridin-3-yl) | oxa-9-azabicyclo[3.3.1]nonan-7-yl-O- | TFA | (1R,5S,7S)-oxa-9-azabicyclo[3.3.1]nonan-7-yl 1-(pyridin-3-yl)-1H-indole-3-carboxylate, 2,2,2-trifluoroacetate | 363.4097 | 364.2 |
| 6 | indol-3-yl with N-(pyridin-3-yl) | 9-(methyl-d₃)-3-oxa-9-azabicyclo[3.3.1]nonan-7-yl-NH- | TFA | N-((1R,5S,7S)-9-methyl-d₃-3-oxa-9-azabicyclo[3.3.1]nonan-7-yl)-1-(pyridin-2-yl)-1H-indole-3-carboxamide, 2,2,2-trifluoroacetate | 379.47 | 380.3 |

| Cpd. No. | (I) | —Z—R¹ | Salt | Name | MW Calcd. | MS Obs. (M + 1)+ |
|---|---|---|---|---|---|---|
| 7 | | | TFA | (1R,5S,7S)-9-methyl-d₃-3-oxa-9-azabicyclo[3.3.1]nonan-7-yl 1-(pyridin-2-yl)-1H-indole-3-carboxylate, 2,2,2-trifluoroacetate | 380.45 | 381.2 |
| 8 | | | TFA | N-((1R,5S,7S)-9-methyl-d₃-3-oxa-9-azabicyclo[3.3.1]nonan-7-yl)-1-(pyridin-2-yl)-1H-indole-3-carboxamide, 2,2,2-trifluoroacetate | 379.47 | 380.3 |
| 9 | | | TFA | (1R,5S,7S)-3-oxa-9-azabicyclo[3.3.3]nonan-7-yl 1-(1-methyl-1H-pyrazol-4-yl)-1H-indole-3-carboxylate, 2,2,2-trifluoroacetic acid salt | 366.414 | 367.15 |
| 10 | | | TFA | N-((1R,5S,7S)-9-methyl-3-oxa-9-azabicyclo[3.3.1]nonan-7-yl)-1-(pyridin-2-yl)-1H-pyrrolo[2,3-b]pyridine-3-carboxamide, 2,2,2-trifluoroacetic acid salt | 377.44 | 378.25 |

-continued

| Cpd. No. | (I) | —Z—R¹ | Salt | Name | MW Calcd. | MS Obs. (M+1)⁺ |
|---|---|---|---|---|---|---|
| 11 | | | TFA | N-((1R,5S,7S)-9-methyl-3-oxa-9-azabicyclo[3.3.1]nonan-7-yl)-1-(pyridin-3-yl)-1H-pyrrolo[2,3-b]pyridine-3-carboxamide, 2,2,2-trifluoroacetic acid salt | 377.44 | 378.25 |
| 12 | | | TFA | 5-fluoro-N-((1R,5S,7S)-9-methyl-3-oxa-9-azabicyclo[3.3.1]nonan-7-yl)-1-(pyridin-2-yl)-1H-pyrrolo[2,3-b]pyridine-3-carboxamide, 2,2,2-trifluoroacetic acid salt | 395.43 | 396.30 |
| 13 | | | TFA | 5-fluoro-N-((1R,5S,7S)-9-methyl-3-oxa-9-azabicyclo[3.3.1]nonan-7-yl)-1-(pyridin-3-yl)-1H-pyrrolo[2,3-b]pyridine-3-carboxamide, 2,2,2-trifluoroacetic acid salt | 395.43 | 396.25 |
| 14 | | | TFA | N-((1R,5S,7S)-9-methyl-3-oxa-9-azabicyclo[3.3.1]nonan-7-yl)-1-(pyridin-2-yl)-1H-indazole-3-carboxamide, 2,2,2-trifluoroacetic acid salt | 377.44 | 378.30 |

-continued

| Cpd. No. | (I) | —Z—R¹ | Salt | Name | MW Calcd. | MS Obs. (M+1)⁺ |
|---|---|---|---|---|---|---|
| 15 | | | TFA | 1-(1-methyl-1H-pyrazol-4-yl)-N-((1R,5S,7S)-9-methyl-3-oxa-9-azabicyclo[3.3.1]nonan-7-yl)-1H-indole-3-carboxamide, 2,2,2-trifluoroacetic acid salt | 379.456 | 380.30 |
| 16 | | | TFA | (1R,5S,7S)-3-oxa-9-azabicyclo[3.3.1]nonan-7-yl 1-(1-methyl-1H-pyrazol-3-yl)-1H-indole-3-carboxylate, 2,2,2-trifluoroacetic acid salt | 366.414 | 367.20 |
| 17 | | | TFA | 1-(1-methyl-1H-pyrazol-3-yl)-N-((1R,5S,7S)-9-methyl-3-oxa-9-azabicyclo[3.3.1]nonan-7-yl)-1H-indole-3-carboxamide, 2,2,2-trifluoroacetic acid salt | 379.456 | 380.25 |
| 18 | | | TFA | (1R,5S,7S)-9-methyl-3-oxa-9-azabicyclo[3.3.1]nonan-7-yl 1-(1-(2-fluoroethyl)-1H-pyrazol-4-yl)-1H-indole-3-carboxylate, 2,2,2-trifluoroacetic acid salt | 412.457 | 413.30 |

-continued

| Cpd. No. | (I) | —Z—R[1] | Salt | Name | MW Calcd. | MS Obs. (M+1)+ |
|---|---|---|---|---|---|---|
| 19 | | | TFA | (1R,5S,7S)-3-oxa-9-azabicyclo[3.3.1]nonan-7-yl 1-(2-cyanopyridin-4-yl)-1H-indole-3-carboxylate, 2,2,2-trifluoroacetic acid salt | 388.419 | 389.20 |
| 20 | | | TFA | N-((1R,5S,7S)-9-methyl-3-oxa-9-azabicyclo[3.3.1]nonan-7-yl)-1-(2-methylpyridin-3-yl)-1H-indole-3-carboxamide, 2,2,2-trifluoroacetic acid salt | 390.478 | 391.30 |
| 21 | | | TFA | N-((1R,5S,7S)-9-methyl-3-oxa-9-azabicyclo[3.3.1]nonan-7-yl)-1-(4-methylpyridin-3-yl)-1H-indole-3-carboxamide, 2,2,2-trifluoroacetic acid salt | 390.478 | 391.25 |
| 22 | | | TFA | (1R,5S,7S)-3-oxa-9-azabicyclo[3.3.1]nonan-7-yl 1-(1-methyl-1H-pyrazol-5-yl)-1H-indole-3-carboxylate, 2,2,2-trifluoroacetic acid salt | 366.414 | 367.25 |

-continued

| Cpd. No. | (I) | —Z—R¹ | Salt | Name | MW Calcd. | MS Obs. (M + 1)+ |
|---|---|---|---|---|---|---|
| 23 | | | TFA | 1-(1-methyl-1H-pyrazol-5-yl)-N-((1R,5S,7S)-9-methyl-3-oxa-9-azabicyclo[3.3.1]nonan-7-yl)-1H-indole-3-carboxamide, 2,2,2-trifluoroacetic acid salt | 379.456 | 380.30 |
| 24 | | | TFA | N-((1R,5S,7S)-9-methyl-3-oxa-9-azabicyclo[3.3.1]nonan-7-yl)-1-(1H-pyrazol-4-yl)-1H-indole-3-carboxamide, 2,2,2-trifluoroacetic acid salt | 365.429 | 366.20 |
| 25 | | | | 1-(1-(difluoromethyl)-1H-pyrazol-4-yl)-N-((1R,5S,7S)-9-methyl-3-oxa-9-azabicyclo[3.3.1]nonan-7-yl)-1H-indole-3-carboxamide | 415.436 | 416.30 |
| 26 | | | TFA | (1R,5S,7S)-9-methyl-3-oxa-9-azabicyclo[3.3.1]nonan-7-yl 1-(1-methyl-1H-pyrazol-4-yl)-1H-indole-3-carboxylate | 380.440 | 381.25 |

-continued

| Cpd. No. | (I) | —Z—R¹ | Salt | Name | MW Calcd. | MS Obs. (M + 1)⁺ |
|---|---|---|---|---|---|---|
| 27 | | | TFA | N-(1R,5S,7S)-3-oxa-9-azabicyclo[3.3.1]nonan-7-yl)-1-(pyridin-3-yl)-1H-indole-3-carboxamide | 362.425 | 363.25 |
| 28 | | | TFA | N-((1R,5S,7S)-3-oxa-9-azabicyclo[3.3.1]nonan-7-yl)-1-(1-methyl-1H-pyrazol-4-yl)-1H-indole-3-carboxamide | 365.429 | 366.25 |
| 29 | | | TFA | (1R,5S,7S)-9-methyl-3-oxa-9-azabicyclo[3.3.1]nonan-7-yl 1-(1H-pyrazol-4-yl)-1H-indole-3-carboxylate | 366.414 | 367.25 |
| 30 | | | TFA | N-((1R,5S,7S)-3-oxa-9-azabicyclo[3.3.1]nonan-7-yl)-1-(1H-pyrazol-4-yl)-1H-indole-3-carboxamide | 351.402 | 352.20 |

-continued

| Cpd. No. | (I) | —Z—R[1] | Salt | Name | MW Calcd. | MS Obs. (M + 1)[+] |
|---|---|---|---|---|---|---|
| 31 | | | TFA | N-((1R,5S,7S)-9-ethyl-3-oxa-9-azabicyclo[3.3.1]nonan-7-yl)-1-(1-methyl-1H-pyrazol-4-yl)-1H-indole-3-carboxamide | 393.482 | 394.35 |
| 32 | | | TFA | 3-(3-(((1R,5S,7S)-9-methyl-3-oxa-9-azabicyclo[3.3.1]nonan-7-yl)carbamoyl)-1H-indol-1-yl)pyridine 1-oxide | 392.451 | 393.30 |

Embodiments:

Embodiment (A)

In one embodiment, the compound of Formula (I) or pharmaceutical salt thereof as defined in the Summary is where Z is O.

Embodiment (B)

In one embodiment, the compound of Formula (I) or pharmaceutical salt thereof as defined in the Summary is where Z is $NR_a$. Within this embodiment, in another group of compounds $R_a$ is hydrogen. Within this embodiment, in another group of compounds $R_a$ is methyl.

Embodiment (C)

In another embodiment, the compound of Formula (I) or pharmaceutical salt thereof as defined in the Summary and embodiments (A) and (B) above and groups contained therein, in one group of compounds $R_1$ is a ring of formula

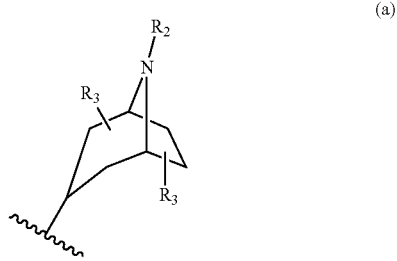

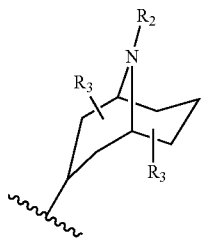

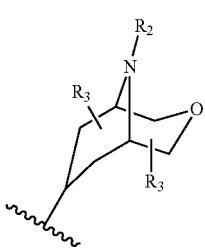

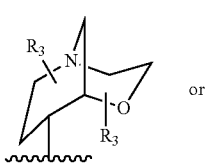

-continued

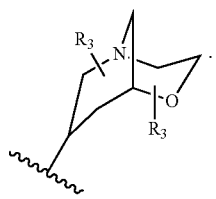
(g)

(a) Within groups in embodiments (C), in one group of compounds $R_1$ is a ring of formula (a) or (d). Within (a), in one embodiment, $R_1$ is a ring of formula

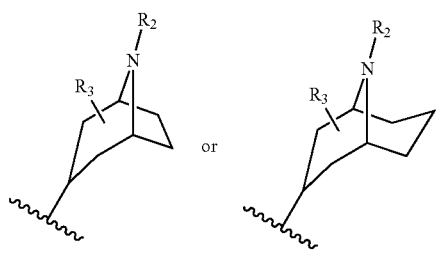
or (b) Within groups in embodiments (C), in another group of compounds $R_1$ is a ring of formula (e), (f) or (g). Within (b), in one group of compounds $R_1$ is a ring of formula (e). Within (b), in one group of compounds $R_1$ is a ring of formula (f) or (g). Within (b), in one group of compounds $R_1$ is a ring of formula

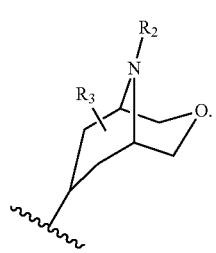

(i) Within groups in embodiments (C) and embodiments contained therein i.e., (a) and (b) and groups contained therein, in one group of compounds each $R_3$ is independently hydrogen or methyl. Within these groups of compounds in one group of compounds each $R_3$ is hydrogen.

(ii) Within groups in embodiments (C) and embodiments contained therein i.e., (a) and (b) and groups contained therein, in one group of compounds each $R_3$ is independently hydrogen or methyl and $R_2$ is hydrogen. Within these groups of compounds in one group of compounds $R_2$ is hydrogen and each $R_3$ is hydrogen.

(iii) Within groups in embodiments (C) and embodiments contained therein i.e., (a) and (b) and groups contained therein, in one group of compounds each $R_3$ is independently hydrogen or methyl and $R_2$ is $C_{1-6}$ alkyl. Within these groups of compounds in one group of compounds $R_2$ is methyl, ethyl, or propyl and each $R_3$ is hydrogen. Within these groups of compounds in one group of compounds $R_2$ is methyl and each $R_3$ is hydrogen.

(iv) Within groups in embodiments (C) and embodiments contained therein i.e., (a) and (b) and groups contained therein, in one group of compounds each $R_3$ is independently hydrogen or methyl and $R_2$ is $C_{1-6}$ haloalkyl. Within these groups of compounds in one group of compounds each $R_2$ is trifluoromethyl, 2-fluoroethyl, or 2,2,2-trifluoroethyl and each $R_3$ is hydrogen. Within these groups of compounds in one group of compounds $R_2$ is trifluoromethyl and each $R_3$ is hydrogen.

(v) Within groups in embodiments (C) and embodiments contained therein i.e., (a) and (b) and groups contained therein, in one group of compounds each $R_3$ is independently hydrogen or methyl.

Embodiment (D)

In another embodiment, the compound of Formula (I) or pharmaceutical salt thereof as defined in the Summary and embodiments (A), and (B) above and groups contained therein, in one group of compounds, is where $R_1$ is a ring of formula

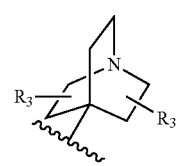
(b)

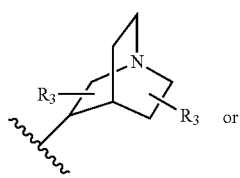
(c)

or

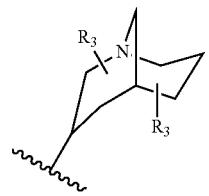
(h)

(a1) Within groups in embodiments (D), in one group of compounds $R_1$ is a ring of formula (c) or (h). Within this embodiment, in one group of compounds the stereochemistry at the chiral carbon is (R) or (S).

(b1) Within groups in embodiments (D), in one group of compounds $R^1$ is a ring of formula (b).

(vi) Within groups in embodiments (D) and embodiments contained therein i.e., (a1) and (b1) and groups contained therein, in one group of compounds each $R_3$ is independently hydrogen or methyl. Within these groups of compounds in one group of compounds each $R_3$ is hydrogen.

Embodiment (E)

In one embodiment, the compound of Formula (I) or pharmaceutical salt thereof as defined in the Summary and embodiments (A), (B), (C), and (D) above and embodiments contained therein, is where $R_4$ is pyridinyl optionally substituted with one or two substituents independently selected from $C_{1-6}$ alkyl, $C_{1-6}$ haloalkyl, $C_{1-6}$ haloalkoxy, $C_{1-6}$ alkoxy, cyano, or halo.

Within the groups in embodiment (E), it is understood that the pyridinyl is represented by the formula below:

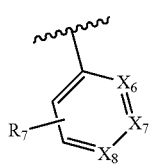

Where one of $X_6$-$X_8$ is N and the one or two optional substituents, $R_7$, are independently selected from $C_{1-6}$ alkyl, $C_{1-6}$ haloalkyl, $C_{1-6}$ haloalkoxy, $C_{1-6}$ alkoxy, cyano, or halo and can be on any carbon atom.

Within the groups in embodiment (E), in another group of compounds $X_6$ is N. Within the groups in embodiment (E), in another group of compounds $X_7$ is N. Within the groups in embodiment (E), in another group of compounds $X_8$ is N.

Embodiment (F)

In one embodiment, the compound of Formula (I) or pharmaceutical salt thereof as defined in the Summary and embodiments (A), (B), (C), and (D) above and embodiments contained therein, is where $R_4$ is pyrazolyl optionally substituted with one or two substituents independently selected from $C_{1-6}$ alkyl, $C_{1-6}$ haloalkyl, $C_{1-6}$ haloalkoxy, $C_{1-6}$ alkoxy, cyano, or halo.

Within the groups in embodiment (F), it is understood that the pyrazolyl is represented by the formula below:

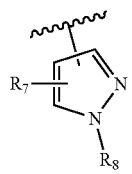

where the $R_4$ pyrazolyl can be attached by any ring carbon and the one or two optional substituents are $R_7$ and $R_8$ where $R_7$, is independently selected from $C_{1-6}$ alkyl, $C_{1-6}$ haloalkyl, $C_{1-6}$ haloalkoxy, $C_{1-6}$ alkoxy, cyano, or halo and can be on any carbon atom and $R_8$ is hydrogen or $C_{1-6}$ alkyl.

Embodiment (G)

In another embodiment, the compound of Formula (I) or pharmaceutical salt thereof as defined in the Summary and embodiments (A), (B), (C), (D), (E), and (F), above and groups contained therein, in one group of compounds, each of $X_1$, $X_2$, $X_3$, and $X_4$ is $CR_5$. Within this embodiment (G), in another group of compounds each $R_5$ is hydrogen.

(c1) Within the groups in embodiment (G), in one group of compounds, $X_5$ is N.

(d1) Within the groups in embodiment (G), in another group of compounds $X_5$ is $CR_6$. Within this group of compounds, in one group $R_6$ is hydrogen Within this embodiment (G), in another group of compounds each $R_5$ is hydrogen. Within the groups in embodiment (G), in another group of compounds one of $R_5$ is fluoro or cyano. Within this group of compounds, in another group the $R_5$ cyano is located at C-5 position, the nitrogen atom substituted with $R_4$ being position 1. Within this group of compounds, in another group of compounds in another group the $R_5$ fluoro is located at C-5 position, the nitrogen atom substituted with $R^4$ being position 1.

Embodiment (H)

In another embodiment, the compound of Formula (I) or pharmaceutical salt thereof as defined in the Summary and embodiments (A), (B), (C), (D), (E), and (F) above and groups is where one of $X_1$, $X_2$, $X_3$, and $X_4$ is N. Within these groups of compounds in one group of compounds $X_1$ is N.

(e1) Within the groups in embodiment (H), in one group of compounds $X_5$ is N.

(f1) Within the groups in embodiment (H), in another group of compounds $X_5$ is $CR_6$ and $R_6$ is hydrogen.

Within the groups in embodiment (H), in one group of compounds each $R_5$ is hydrogen.

Within the groups in embodiment (H), (e1) and (f1), in another group of compounds one of $R_5$ is fluoro, or cyano. Within this group of compounds, in another group the $R_5$ cyano is located at C-5 position, the nitrogen atom substituted with $R_4$ being position 1. Within this group of compounds, in another group of compounds in another group the $R_5$ fluoro is located at C-5 position, the nitrogen atom substituted with $R_4$ being position 1.

General Synthetic Scheme

Compounds of this invention can be made by the methods depicted in the reaction schemes shown below and other methods known in the art.

The starting materials and reagents used in preparing these compounds are either available from commercial suppliers such as Aldrich Chemical Co., (Milwaukee, Wis.), Bachem (Torrance, Calif.), or Sigma (St. Louis, Mo.) or are prepared by methods known to those skilled in the art following procedures set forth in references such as Fieser and Fieser's Reagents for Organic Synthesis, Volumes 1-17 (John Wiley and Sons, 1991); Rodd's Chemistry of Carbon Compounds, Volumes 1-5 and Supplementals (Elsevier Science Publishers, 1989); Organic Reactions, Volumes 1-40 (John Wiley and Sons, 1991), March's Advanced Organic Chemistry, (John Wiley and Sons, 4th Edition) and Larock's Comprehensive Organic Transformations (VCH Publishers Inc., 1989). These schemes are merely illustrative of some methods by which the compounds of this invention can be synthesized, and various modifications to these schemes can be made and will be suggested to one skilled in the art having referred to this disclosure. The starting materials and the intermediates, and the final products of the reaction may be isolated and purified if desired using conventional techniques, including but not limited to filtration, distillation, crystallization, chromatography and the like. Such materials may be characterized using conventional means, including physical constants and spectral data.

Unless specified to the contrary, the reactions described herein take place at atmospheric pressure over a temperature range from about −78° C. to about 150° C., more preferably from about 0° C. to about 12° C. and most preferably at about room (or ambient) temperature, e.g., about 20° C.

Compounds of Formula (I) can be prepared as illustrated and described in Scheme A below.

Scheme A

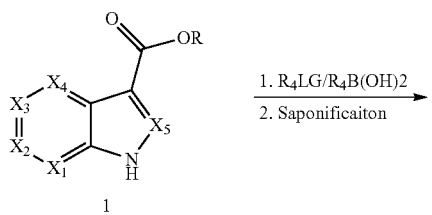

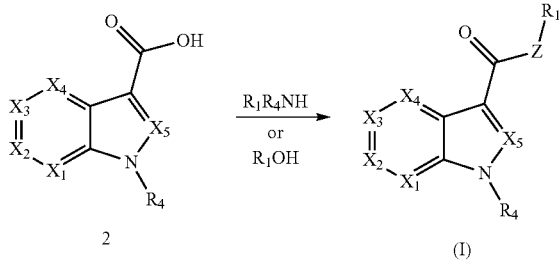

Step 1 involves formation of the C—N bond between $R_4$ and N-1 nitrogen of the compound of formula 1 where R is an acid protecting group such as $C_{1-6}$ alkyl. Compounds of formula 1, $R_4LG$, wherein LG is a leaving group such as sulfonate or halo, and $R_4B(OH)_2$, or ester thereof, are either commercially available or they can be prepared by methods well known in the art. For example 5-fluoro-2-methylindole-3-carboxylic acid ethyl ester, 4,5-difluoro-2-methylindole-3-carboxylic acid ethyl ester, 1H-indole-3-carboxylic acid, 5-methoxy-, methyl ester, 5-fluoro-1H-indole-3-carboxylic acid methyl ester, ethyl 5-methyl-1H-indole-3-carboxylate, 4,5-difluoro-2-methylindole-3-carboxylic acid ethyl ester, 5-cyano-2-methyl-1H-indole-3-carboxylic acid methyl ester, 1H-pyrazolo[3,4-b]pyridine-3-carboxylic acid, 5-fluoro-, methyl ester, 1H-pyrrolo[2,3-b]pyridine-3-carboxylic acid, 5-methyl-, methyl ester, 1H-pyrrolo[2,3-b]pyridine-3-carboxylic acid, 5-fluoro-, methyl ester are commerically available.

Hydrolysis of the ester group under basic aqueous conditions provides the corresponding compound of formula 2. Compound 2 is then converted to a compound of Formula (I) where Z is $NR_a$ or O or nitrogen protected derivative thereof, by forming an activated acid derivative of compound 2, followed by reaction with $R_1R_aNH$ or $R_1OH$ where $R_1$ is as defined in the Summary or nitrogen protected derivative thereof. For example, the activated acid derivative can be mixed anhydride such as with a mixture of TFAA and TFA in toluene or CDI or $Boc_2O$; or acid halide such as with oxalyl chloride, thionyl chloride; or under standard using standard peptide coupling reagents such as HATU in the presence of a base such as N,N-diisopropylethylamine, and a solvent, such as DMF and the like. When nitrogen protected derivative of $R_1R_aNH$ or $R_1OH$ are used, removal of the protecting group provides the compound of Formula (I). Amines and alcohols of formula $R_1R_aNH$ or $R_1OH$ or nitrogen protected derivative thereof are either commercially available or they can be prepared by methods known in the art e.g (1S,5R,6S)-4-oxa-1-azabicyclo[3.3.1]nonan-6-ol can be prepared as described in Journal of Medicinal Chemistry, 1993, 36, 683-689.

Alternatively, compound of Formula I can be synthesized by first coupling the acid derivative of compound 1 (R is H) with $R_1R_aNH$ or $R_1OH$ as described above, followed by formation of N—C bond as described in Step 1 of Scheme A above.

Detailed descriptions of synthesis of compounds of Formula (I) via above procedures are provided in Working Examples below.

Utility

5-HT3 receptors are known to be expressed in the central nervous system in regions involving vomiting reflex, processing of pain, cognition and anxiety control and play a role in the pathogenesis of diseases such as emesis, migraine, drug addiction, and neurodegenerative and psychiatric disorders such as anxiety and depression (see Hewlett et al., 2003 *J. Clin. Psychiatry* 64, 1025-1030; Kelley et al., 2003a, *Eur J Pharmacol.*, 461, 19-25; Haus et al., 2000 *Scand J Rheumatol Suppl* 113, 55-58; and Faris et al., 2006 *J affect Disorder* 92, 79-90), eating disorders (Hammer et al., 1990 *Am J Physiol* 259, R627-R636, and Jiang & Gietzen 1994 *Pharmacol Biochem Behav* 47, 59-63), schizophrenia (see Hermann et al. 1996 *Biochem Biophys Res Commun* 225, 957-960; Sirota et al., 2000 *Am J Psychiatry* 157, 287-289; Adler et al., 2005 *Am J Psychiatry* 162, 386-388; Koike et al., Levkovitz et al, 2005 *Schizophr Res* 76, 67-72), cognitive dysfunction associated with schizophrenia (see Zhang et al., 2006 *Schizophr Res* 88, 102-110; Akhondzadeh et al., 2009 *Schizophr Res* 107, 206-212), congnitive dysfuntion associated with Parkinson's disease, Huntington's Chorea, presenile dementias and Alzheimer's disease (see Costall and Naylor 2004 *CNS Neurol Disord* 3, 27-37) substance abuse and addiction (see Johnson et al., 2002 *Psychopharmacology* (Berl) 160, 408-413; Johnson, 2004 *CNS Drugs* 18, 1105-1118; Dawes et al., 2005 *Addict Behav* 30, 1630-1637, Johnson 2006 *Drug Alcohol Depend* 84, 256-263), and pain (see Kayser et al, 2007 *Pain* 130, 235; Glaum et al., 1998 *Neurosci Lett* 95, 313-317; Schworer & Ramadori 1993 *Clin Investig* 71, 659; Thompson and Lummis 2007 *Exp Opin Ther Targets,* 11, 527-540). In addition, 5-HT3 receptors are expressed in the GI tract and hence may play a role in GI disorders such as dyspepsia, gastroesophagal reflux disease and irritable bowel syndrome (see Graeff 1997 *Psychiatr Clin North Am* 20, 723; Thompson and Lummis 2007 *Exp Opin Ther Targets,* 11, 527-540; Barnes et al. 2009 *Neuropharmacology* 56, 273). Expression of the 5-HT3A subsunit has also been discovered extraneuronally in immune cells such as monocyes, chondrocytes, T-cells, synovial tissue and platelets (Fiebich et al., 2004 *Scan J Rheumatol Suppl,* 9-11, Stratz et al., 2008 *Thromb Haemost* 99, 784) and of 5-HT3A, C-E within the lamina propia in the epithelium of the gut mucose (Kapeller et al., *J Comp Neuro.,* 2008; 509: 356-371) thus suggesting they may be involved in immunological and inflammatory diseases like atherosclerosis, tendomyopathies and fibromyalgia.

Testing

The 5-HT3 inhibitory activity of the compounds of the present invention can be tested using the in vitro assay and in vivo assay described in Biological Example 1, 2, and 3 below.

Administration and Pharmaceutical Composition

In general, the compounds of this invention will be administered in a therapeutically effective amount by any of the accepted modes of administration for agents that serve similar utilities. Therapeutically effective amounts of compounds of Formula (I) may range from about 0.01 to about 75 mg per kg patient body weight per day, which can be administered in single or multiple doses. Preferably, the dosage level will be about 0.01 to about 10 mg/kg per day; more preferably about 0.5 to about 5 mg/kg per day or 0.1-2 mg/kg/day. For oral administration, the compositions are preferably provided in the form of tablets containing about 0.5 to about 200 milligrams of the active ingredient, from about 0.5, 1.0, 5.0, 10, 15, 20, 25, 50, 75, 100, 150, or 200 milligrams of the active ingredient. The actual amount of the compound of this invention, i.e., the active ingredient, will depend upon numerous factors such as the severity of the disease to be treated, the age and relative health of the subject, the potency of the compound utilized, the route and form of administration, and other factors. Although these dosages are based on an average human subject having a mass of about 60 kg to about 70 kg, the physician will be able to determine the appropriate dose for a patient (e.g., an infant) whose mass falls outside of this weight range.

In general, compounds of this invention will be administered as pharmaceutical compositions by any one of the following routes: oral, systemic (e.g., transdermal, intranasal or by suppository), or parenteral (e.g., intramuscular, intravenous or subcutaneous) administration. The preferred manner of administration is oral using a convenient daily dosage regimen, which can be adjusted according to the degree of affliction. Compositions can take the form of tablets, pills, capsules, semisolids, powders, sustained release formulations, solutions, suspensions, elixirs, aerosols, or any other appropriate compositions.

The choice of formulation depends on various factors such as the mode of drug administration (e.g., for oral administration, formulations in the form of tablets, pills or capsules are preferred) and the bioavailability of the drug substance. Recently, pharmaceutical formulations have been developed especially for drugs that show poor bioavailability based upon the principle that bioavailability can be increased by increasing the surface area i.e., decreasing particle size. For example, U.S. Pat. No. 4,107,288 describes a pharmaceutical formulation having particles in the size range from 10 to 1,000 nm in which the active material is supported on a crosslinked matrix of macromolecules. U.S. Pat. No. 5,145,684 describes the production of a pharmaceutical formulation in which the drug substance is pulverized to nanoparticles (average particle size of 400 nm) in the presence of a surface modifier and then dispersed in a liquid medium to give a pharmaceutical formulation that exhibits remarkably high bioavailability.

The compositions are comprised of in general, a compound of formula (I) in combination with at least one pharmaceutically acceptable excipient. Acceptable excipients are non-toxic, aid administration, and do not adversely affect the therapeutic benefit of the compound of formula (I). Such excipient may be any solid, liquid, semi-solid or, in the case of an aerosol composition, gaseous excipient that is generally available to one of skill in the art.

Solid pharmaceutical excipients include starch, cellulose, talc, glucose, lactose, sucrose, gelatin, malt, rice, flour, chalk, silica gel, magnesium stearate, sodium stearate, glycerol monostearate, sodium chloride, dried skim milk and the like. Liquid and semisolid excipients may be selected from glycerol, propylene glycol, water, ethanol and various oils, including those of petroleum, animal, vegetable or synthetic origin, e.g., peanut oil, soybean oil, mineral oil, sesame oil, etc. Preferred liquid carriers, particularly for injectable solutions, include water, saline, aqueous dextrose, and glycols.

Compressed gases may be used to disperse a compound of this invention in aerosol form. Inert gases suitable for this purpose are nitrogen, carbon dioxide, etc.

Other suitable pharmaceutical excipients and their formulations are described in Remington's Pharmaceutical Sciences, edited by E. W. Martin (Mack Publishing Company, 18th ed., 1990).

The level of the compound in a formulation can vary within the full range employed by those skilled in the art. Typically, the formulation will contain, on a weight percent (wt %) basis, from about 0.01-99.99 wt % of a compound of formula (I) based on the total formulation, with the balance being one or more suitable pharmaceutical excipients. Preferably, the compound is present at a level of about 1-80 wt %.

The compounds of the present invention may be used in combination with one or more other drugs in the treatment of diseases or conditions for which compounds of the present invention or the other drugs may have utility, where the combination of the drugs together are safer or more effective than either drug alone. Such other drug(s) may be administered, by a route and in an amount commonly used therefore, contemporaneously or sequentially with a compound of the present invention. When a compound of the present invention is used contemporaneously with one or more other drugs, a pharmaceutical composition in unit dosage form containing such other drugs and the compound of the present invention can be used. However, the combination therapy may also include therapies in which the compound of the present invention and one or more other drugs are administered on different overlapping schedules. It is also contemplated that when used in combination with one or more other active ingredients, the compounds of the present invention and the other active ingredients may be used in lower doses than when each is used singly.

Accordingly, the pharmaceutical compositions of the present invention also include those that contain one or more other active ingredients, in addition to a compound of the present invention.

The above combinations include combinations of a compound of the present invention not only with one other active compound, but also with two or more other active compounds. Likewise, compounds of the present invention may be used in combination with other drugs that are used in the prevention, treatment, control, amelioration, or reduction of risk of the diseases or conditions for which compounds of the present invention are useful. Such other drugs may be administered, by a route and in an amount commonly used therefore, contemporaneously or sequentially with a compound of the present invention. Accordingly, the pharmaceutical compositions of the present invention also include those that also contain one or more other active ingredients, in addition to a compound of the present invention. The weight ratio of the compound of the present invention to the second active ingredient may be varied and will depend upon the effective dose of each ingredient. Generally, an effective dose of each will be used.

In one embodiment, the compound of the present invention may be administered in combination with anti-Alzheimer's agents, beta-secretase inhibitors, gamma-secretase inhibitors, HMG-CoA reductase inhibitors, NSAID's including ibuprofen, vitamin E, and anti-amyloid antibodies. In another embodiment, the compound of the present invention may be administered in combination with sedatives, hypnotics, anxiolytics, antipsychotics, antianxiety agents, cyclopyrrolones, imidazopyridines, pyrazolopyrimidines, minor tranquilizers, melatonin agonists and antagonists, melatonergic agents, benzodiazepines, barbiturates, mGlu2/3 agonists, 5HT-2 antagonists, PDE10 antagonists, GlyT1 inhibitors, and the like, such as: adinazolam, allobarbital, alonimid, alprazolam, amisulpride, amitriptyline, amobarbital, amoxapine, aripiprazole, bentazepam, benzoctamine, brotizolam, bupropion, busprione, butabarbital, butalbital, capuride, carbocloral, chloral betaine, chloral hydrate, clomipramine, clonazepam, cloperidone, clorazepate, chlordiazepoxide, clorethate, chlorpromazine, clozapine, cyprazepam, desipramine, dexclamol, diazepam, dichloralphenazone, divalproex, diphenhydramine, doxepin, estazolam, ethchlorvynol, etomidate, fenobam, flunitrazepam, flupentixol, fluphenazine, flurazepam, fluvoxamine, fluoxetine, fosazepam, glutethimide, halazepam, haloperidol, hydroxyzine, imipramine, lithium, lorazepam, lormetazepam, maprotiline, mecloqualone, melatonin, mephobarbital, meprobamate, methaqualone, midaflur, midazolam, nefazodone, nisobamate, nitrazepam, nortriptyline, olanzapine, oxazepam, paraldehyde, paroxetine, pentobarbital, perlapine, perphenazine, phenelzine, phenobarbital, prazepam, promethazine, propofol, protriptyline, quazepam, quetiapine, reclazepam, risperidone, roletamide, secobarbital, sertraline, suproclone, temazopam, thioridazine, thiothixene, tracazolate, kanylcypromaine, trazodone, triazolam, trepipam, tricetamide, triclofos, trifluoperazine, trimetozine, trimipramine, uldazepam, venlafaxine, zaleplon, ziprasidone, zolazepam, zolpidem, [4-(3-fluoro-5-trifluoromethylpyridin-2-yl)piperazin-1-yl][5-methanesulfonyl-2-((S)-2,2,2-trifluoro-1-methylethoxy)phenyl]methanone (RG1678), glyt1 inhibitors disclosed in U.S. Pat. No. 7,538,114, Table 1 in column 14, and salts thereof, and combinations thereof.

In another embodiment, the compound of the present invention may be administered in combination with levodopa (with or without a selective extracerebral decarboxylase inhibitor such as carbidopa or benserazide), anticholinergics such as biperiden (optionally as its hydrochloride or lactate salt) and trihexyphenidyl (benzhexol) hydrochloride, COMT inhibitors such as entacapone, MOA-B inhibitors, antioxidants, A2a adenosine receptor antagonists, cholinergic agonists, NMDA receptor antagonists, serotonin receptor antagonists and dopamine receptor agonists such as alentemol, bromocriptine, fenoldopam, lisuride, naxagolide, pergolide and pramipexole. It will be appreciated that the dopamine agonist may be in the form of a pharmaceutically acceptable salt, for example, alentemol hydrobromide, bromocriptine mesylate, fenoldopam mesylate, naxagolide hydrochloride and pergolide mesylate. Lisuride and pramipexol are commonly used in a non-salt form.

In another embodiment, the compound of the present invention may be administered in combination with a compound from the phenothiazine, thioxanthene, heterocyclic dibenzazepine, butyrophenone, diphenylbutylpiperidine and indolone classes of neuroleptic agent. Suitable examples of phenothiazines include chlorpromazine, mesoridazine, thioridazine, acetophenazine, fluphenazine, perphenazine and trifluoperazine. Suitable examples of thioxanthenes include chlorprothixene and thiothixene. An example of a dibenzazepine is clozapine. An example of a butyrophenone is haloperidol. An example of a diphenylbutylpiperidine is pimozide. An example of an indolone is molindolone. Other neuroleptic agents include loxapine, sulpiride and risperidone. It will be appreciated that the neuroleptic agents when used in combination with the subject compound may be in the form of a pharmaceutically acceptable salt, for example, chlorpromazine hydrochloride, mesoridazine besylate, thioridazine hydrochloride, acetophenazine maleate, fluphenazine hydrochloride, flurphenazine enathate, fluphenazine decanoate, trifluoperazine hydrochloride, thiothixene hydrochloride, haloperidol decanoate, loxapine succinate and molindone hydrochloride. Perphenazine, chlorprothixene, clozapine, haloperidol, pimozide and risperidone are commonly used in a non-salt form. Thus, the compound of the present invention may be administered in combination with acetophenazine, alentemol, aripiprazole, amisulpride, benzhexol, bromocriptine, biperiden, chlorpromazine, chlorprothixene, clozapine, diazepam, fenoldopam, fluphenazine, haloperidol, levodopa, levodopa with benserazide, levodopa with carbidopa, lisuride, loxapine, mesoridazine, molindolone, naxagolide, olanzapine, pergolide, perphenazine, pimozide, pramipexole, quetiapine, risperidone, sulpiride, tetrabenazine, trihexyphenidyl, thioridazine, thiothixene, trifluoperazine or ziprasidone.

In another embodiment, the compound of the present invention may be administered in combination with an anti-depressant or anti-anxiety agent, including norepinephrine reuptake inhibitors (including tertiary amine tricyclics and secondary amine tricyclics), selective serotonin reuptake inhibitors (SSRIs), monoamine oxidase inhibitors (MAOIs), reversible inhibitors of monoamine oxidase (RIMAs), serotonin and noradrenaline reuptake inhibitors (SNRIs), corticotropin releasing factor (CRF) antagonists, adrenoreceptor antagonists, neurokinin-1 receptor antagonists, atypical anti-depressants, benzodiazopines, 5-HTA agonists or antagonists, especially 5-HTA partial agonists, and corticotropin releasing factor (CRF) antagonists. Specific agents include: amitriptyline, clomipramine, doxepin, imipramine and trimipramine; amoxapine, desipramine, maprotiline, nortriptyline and protriptyline; fluoxetine, fluvoxamine, paroxetine and sertraline; isocarboxazid, phenelzine, tranylcypromine and selegiline; moclobemide, venlafaxine; duloxetine; aprepitant; bupropion, lithium, nefazodone, trazodone and viloxazine; alprazolam, chlordiazepoxide, clonazopam, chlorazepate, diazopam, halazepam, lorazepam, oxazopam and prazepam; buspirone, flesinoxan, gepirone and ipsapirone, and pharmaceutically acceptable salts thereof.

EXAMPLES

The following preparations of compounds of Formula (I) are given to enable those skilled in the art to more clearly understand and to practice the present invention. They should not be considered as limiting the scope of the invention, but merely as being illustrative and representative thereof.

Synthetic Procedures

Reference 1

Synthesis of (1R,5S,7S)-tert-butyl 7-hydroxy-3-oxa-9-azabicyclo[3.3.1]nonane-9-carboxylate

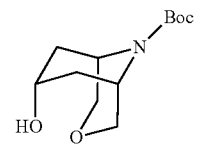

Sodium borohydride (259 mg, 6.84 mmol) was added portion-wise to a solution of (1R,5S)-tert-butyl 7-oxo-3-oxa-9-azabicyclo[3.3.1]nonane-9-carboxylate (550 mg, 2.279 mmol) in MeOH (4559 µl) at 0° C. After 5 min, the reaction mixture was allowed to warm to RT then stirred for 30 min. The mixture was concentrated under reduced pressure, dissolved in EtOAc and washed with brine. The combined organic layers were dried over anhydrous Na$_2$SO$_4$, filtered and concentrated under reduced pressure to afford the title compound as a white solid, which was used without further purification.

Reference 2

Synthesis of (1R,5S,7S)-9-methyl-d₃-oxa-9-azabicyclo[3.3.1]nonan-7-amine

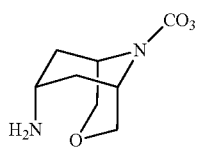

Step 1: (1R,5S)-9-Methyl-d₃-oxa-9-azabicyclo[3.3.1]nonan-7-one

To a solution of sodium dihydrogenphosphate hydrate (22.30 g, 162 mmol) and 2-hydroxypropane-1,2,3-tricarboxylic acid (4.90 g, 25.5 mmol) in water (Volume: 506 ml) was added in turn methyl-d₃-amine hydrogen chloride (5 g, 70.9 mmol) and 3-oxopentanedioic acid (11.91 g, 82 mmol). The pH was adjusted to 4.6 with a 10% aqueous solution of NaOH. A solution of 2,2'-oxydiacetaldehyde (3.62 g, 35.4 mmol) in 8 mL MeOH was added at RT and the resulting mixture was stirred at RT for 3 days. 10% aqueous NaOH was used to basify the reaction solution, and extracted with DCM (100 mL). Purification with column chromatography (SiO₂, DCM/MeOH) gave the title compound as a white solid.

Step 2: (1R,5S)-9-methyl-d₃-3-oxa-9-azabicyclo[3.3.1]nonan-7-one oxime

A solution of (1R,5S)-9-methy-d₃-oxa-9-azabicyclo[3.3.1]nonan-7-one (1.65 g, 10.43 mmol), hydroxylamine hydrochloride (0.761 g, 10.95 mmol) and pyridine (0.843 ml, 10.43 mmol) in EtOH (Volume: 52.1 ml) was heated at 75° C. for 3 h. After 0.2 mL of triethylamine was added to the reaction solution, the solvent was removed. Purification by column chromatography (SiO₂; DCM/MeOH) gave the title compound as a white solid.

Step 3: (1R,5S,7S)-9-Methyl-d₃-oxa-9-azabicyclo[3.3.1]nonan-7-amine

Sulfuric acid (1.108 ml, 20.78 mmol) was added dropwise over 15 min to a well-stirred solution of aluminum(III) lithium hydride (1.0 M in THF, 41.6 ml, 41.6 mmol) in THF (Volume: 41.6 ml) at 0° C. The mixture was stirred for another hour at 0° C. and then (1R,5S)-9-methyl-d3-3-oxa-9-azabicyclo[3.3.1]nonan-7-one oxime (1.8 g, 10.39 mmol) was added portionwise at 0° C. The reaction mixture was heated under reflux (80° C.) for 1.5 h. To the well-stirred reaction mixture, 1.58 mL of water, 2.37 mL of 10 M NaOH and 3.95 mL of water were subsequently added at 0° C. The resultant suspension was filtered through a pad of Celite and washed with THF. The combined organic phase was concentrated under reduced pressure to afford the title compound as a pale-yellow oil, which was used without further purification.

Reference 3

Synthesis of (1R,5S,7S)-9-(trifluoromethyl)-3-oxa-9-azabicyclo[3.3.1]nonan-7-amine 2,2,2-trifluoroacetate

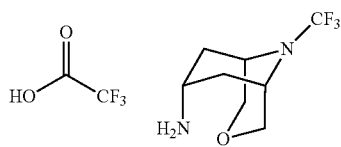

Step 1: Benzyl (1R,5S,7S)-3-oxa-9-azabicyclo[3.3.1]nonan-7-ylcarbamate

Benzyl chloroformate (330 µl, 2.319 mmol) was added to a solution of (1R,5S,7S)-tert-butyl 7-amino-3-oxa-9-azabicyclo[3.3.1]nonane-9-carboxylate 2,2,2-trifluoroacetate (751.3 mg, 2.108 mmol) and triethylamine (619 µl, 4.43 mmol) in DCM (10 ml) at RT. After 14 h, trifluoroacetic acid (2.4 mL, 31.6 mmol) was added to the reaction mixture. After 15 min, the mixture was concentrated, dissolved with DMF, filtered, and purified by HPLC followed by neutralization (K₂CO₃) to afford the title compound as a colorless oil.

Step 2: Benzyl ((1R,5S,7S)-9-(trifluoromethyl)-3-oxa-9-azabicyclo[3.3.1]nonan-7-yl)carbamate A solution of benzyl (1R,5S,7S)-3-oxa-9-azabicyclo[3.3.1]nonan-7-ylcarbamate (27 mg, 0.098 mmol) and dibromodifluoromethane (18.06 µl, 0.195 mmol) in DMSO (489 µl) was treated with tetrakis(dimethylamino)ethylene (50.1 µl, 0.215 mmol), dropwise at 0° C. The mixture slowly warmed to RT overnight then was poured into a 1:1 mixture of NaHCO₃/Na₂S₂O₃ and extracted twice with Et₂O. The combined extracts were concentrated and purified by prep-TLC to give the title compound as a yellow oil.

Step 3: (1R,5S,7S)-9-(Trifluoromethyl)-3-oxa-9-azabicyclo[3.3.1]nonan-7-amine 2,2,2-trifluoroacetate In a vial containing benzyl ((1R,5S,7S)-9-(trifluoromethyl)-3-oxa-9-azabicyclo[3.3.1]nonan-7-yl)carbamate (10 mg, 0.029 mmol), palladium on carbon (10 wt %, 1.020 mg, 9.58 µmol), and TFA (4.47 µl, 0.058 mmol) in MeOH (Volume: 145 µl) was purged with hydrogen gas and left under 1 atm H₂ atmosphere for 2 h. Filtration through a pad of Celite/MgSO₄ (1:1) followed by concentration gave the title compound as a colorless film, which was used without further purification.

Reference 4

Synthesis of (1S,5R,6S)-4-oxa-1-azabicyclo[3.3.1]nonan-6-ol, (1R,5S,6R)-4-oxa-1-azabicyclo[3.3.1]nonan-6-ol

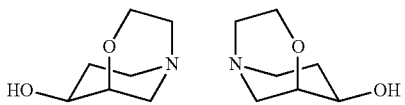 [SMILES: OC1CCN2CCOC1C2 ; OC1CCN2CCOC1C2]

Step 1: Ethyl 4-(3-ethoxy-3-oxopropyl)morpholine-2-carboxylate

A mixture of ethyl morpholine-2-carboxylate (3 g, 18.85 mmol) and ethyl acrylate (5 ml, 18.85 mmol) was heated at 100° C. for 14 h. The reaction was cooled to RT then diluted with Et$_2$O and extracted with aqueous 3M HCl. The combined aqueous layers were basified by solid K$_2$CO$_3$ and extracted with DCM. The combined organic layers were dried over anhydrous Na$_2$SO$_4$, filtered and concentrated under reduced pressure to afford the title compound as a pale-yellow oil, which was used without further purification.

Step 2: (1S,5R)-4-Oxa-1-azabicyclo[3.3.1]nonan-6-one (1R,5S)-4-Oxa-1-azabicyclo[3.3.1]nonan-6-one A solution of ethyl 4-(3-ethoxy-3-oxopropyl)morpholine-2-carboxylate (3.07 g, 11.84 mmol) in toluene (8 ml) was added to a suspension of potassium 2-methylpropan-2-olate (3.65 g, 32.6 mmol) in toluene (39.5 ml) at 120° C. After being stirred at 120° C. for 3 h, the reaction mixture was cooled to RT and extracted with water (20 mL). The aqueous layer was treated with conc. HCl (20 ml, 240 mmol) then heated at 110° C. for 14 h. The reaction mixture was cooled to RT then concentrated under reduced pressure. The resulting solid was taken up in saturated aq. K$_2$CO$_3$ and extracted with DCM. The combined organic layers were dried over anhydrous Na$_2$SO$_4$, filtered and concentrated under reduced pressure to afford the title compounds as a brown oil, which was used without further purification.

Step 3: (1S,5R,6S)-4-Oxa-1-azabicyclo[3.3.1]nonan-6-ol, (1R,5S,6R)-4-Oxa-1-azabicyclo[3.3.1]nonan-6-ol Sodium borohydride (53.6 mg, 1.417 mmol) was added to a solution of (1S,5R)-4-oxa-1-azabicyclo[3.3.1]nonan-6-one and (1R,5S)-4-oxa-1-azabicyclo[3.3.1]nonan-6-one (100 mg, 0.708 mmol) in MeOH (3542 µl) at 0° C. The reaction mixture was stirred at RT for 30 min, then concentrated under reduced pressure. The residue was taken up in EtOAc and washed with brine. The organic layer was dried over anhydrous Na$_2$SO$_4$, filtered and concentrated under reduced pressure to afford the title compounds as a yellow oil, which was used without further purification

Reference 5

Synthesis of 1-(pyridin-4-yl)-1H-indole-3-carboxylic acid

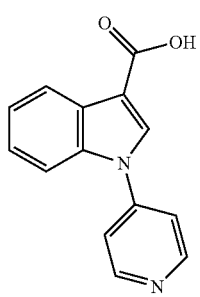 [SMILES: O=C(O)c1cn(-c2ccncc2)c2ccccc12]

Step 1: Methyl 1-(pyridin-4-yl)-1H-indole-3-carboxylate

To a vial containing methyl 1H-indole-3-carboxylate (402 mg, 2.297 mmol), pyridin-4-ylboronic acid (847 mg, 6.89 mmol), copper (II) acetate (542 mg, 2.99 mmol), 4 Å molecular sieves (4 g) and 1,10-phenanthroline (828 mg, 4.59 mmol) were added DCM (9 ml) and triethylamine (0.320 ml, 2.297 mmol). The mixture was stirred at RT for 4 days then filtered through a pad of Celite (washed with MeOH). Evaporation and purification by HPLC (after dilution with DMF and filtration) afforded the title compound as a yellow solid.

Step 2: 1-(Pyridin-4-yl)-1H-indole-3-carboxylic acid

To a solution of methyl 1-(pyridin-4-yl)-1H-indole-3-carboxylate (92 mg, 0.365 mmol) in water (365 µl) and MeOH (365 µl) was added KOH (102 mg, 1.823 mmol). The mixture was heated at 90° C. for 1 h then the MeOH was removed under reduced pressure. The residual aqueous layer was neutralized with 1M HCl (pH=6-7) then extracted with EtOAc. The combined organic layers were dried over anhydrous MgSO$_4$, filtered, concentrated to afford the title compound as a yellow solid, which was used without further purification.

Proceeding as described above, 1-(pyridin-3-yl)-1H-indole-3-carboxylic acid was prepared.

Reference 6

Synthesis of 1-(pyridin-2-yl)-1H-indole-3-carboxylic acid

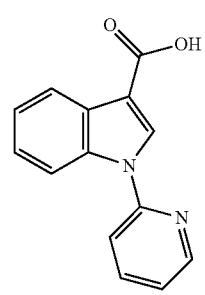 [SMILES: O=C(O)c1cn(-c2ccccn2)c2ccccc12]

Step 1: Methyl 1-(pyridin-2-yl)-1H-indole-3-carboxylate

Sodium hydride (45.7 mg, 1.142 mmol, 60% dispersion in mineral oil) was added to a solution of methyl 1H-indole-3-carboxylate (200 mg, 1.142 mmol) in DMF (2283 µl) at RT. After 30 min, 2-fluoropyridine (99 µl, 1.142 mmol) was added to the mixture and the resulting suspension was heated at 120° C. for 14 h. The reaction mixture was diluted with DMF, filtered, and purified by HPLC to afford the title compound as a white solid.

Step 2: 1-(Pyridin-2-yl)-1H-indole-3-carboxylic acid

The title compound was synthesized by utilizing similar conditions as described in Reference 5, Step 2.

Reference 7

Synthesis of (1R,5S,7S)-9-methyl-3-oxa-9-azabicyclo[3.3.1]nonan-7-yl 1H-indole-3-carboxylate

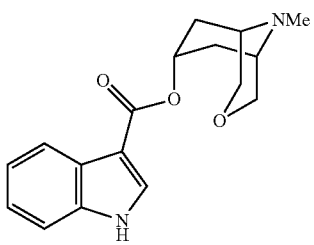 [SMILES: CN1C2COCC1CC(OC(=O)c1c[nH]c3ccccc13)C2]

To a solution of 1H-indole-3-carboxylic acid (250 mg, 1.551 mmol) in PhMe (5171 µl) was added TFAA (219 µl, 1.551 mmol) then TFA (1293 µl). The mixture was stirred for 30 min then commercially available (1R,5S,7S)-9-methyl-3-oxa-9-azabicyclo[3.3.1]nonan-7-ol (203 mg, 1.293 mmol) was added. The reaction mixture stirred at RT for 1 h then was poured into aq NaHCO₃ and stirred until pH=7 and bubbling stopped. The reaction mixture was extracted with EtOAc and dried over MgSO₄. Purification by ISCO (0-20% MeOH/DCM) yielded the title compound as a pink solid.

Reference 8

Synthesis of (1R,5S,7S)-tert-butyl 7-((1H-indole-3-carbonyl)oxy)-3-oxa-9-azabicyclo[3.3.1]nonane-9-carboxylate

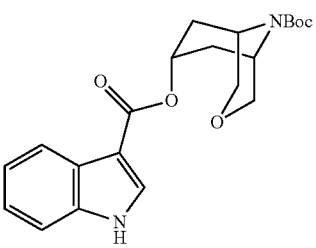 [SMILES: CC(C)(C)OC(=O)N1C2COCC1CC(OC(=O)c1c[nH]c3ccccc13)C2]

Step 1: (1R,5S,7S)-9-benzyl-3-oxa-9-azabicyclo[3.3.1]nonan-7-ol

Sodium borohydride (24.54 g, 649 mmol) was added portionwise over 30 min to a suspension of (1R,5S)-9-benzyl-3-oxa-9-azabicyclo[3.3.1]nonan-7-one (50 g, 216 mmol) in MeOH (540 ml) and THF (540 ml) at 0° C. The mixture was allowed to gradually warm to RT over 1 h. After an additional hour at RT, the mixture was concentrated and the white residue was partitioned between ethyl acetate and brine. The combined organic layers were dried over Na₂SO₄, filtered and concentrated under reduced pressure to afford the title compound as a white solid, which was used without further purification.

Step 2: (1R,5S,7S)-9-benzyl-3-oxa-9-azabicyclo[3.3.1]nonan-7-ol 2,2,2-Trifluoroacetic anhydride (34.5 ml, 244 mmol) and TFA (123 ml) were subsequently added to a solution of 1H-indole-3-carboxylic acid (39.4 g, 244 mmol) in toluene (987 ml) at RT. After 30 min, (1R,5S,7S)-9-benzyl-3-oxa-9-azabicyclo[3.3.1]nonan-7-ol (51.8 g, 222 mmol) was added to the mixture in one portion at RT. After 2 h, the mixture was concentrated under reduced pressure to the half of the original volume. Then, 800 mL of 10% Na₂CO₃ (aq) was added. The mixture was concentrated under reduced pressure until most of the organic solvent was removed. The product was extracted with ethyl acetate and the combined organic layers were washed with brine, dried over Na₂SO₄, filtered and concentrated under reduced pressure. The residual dark purple solid was triturated with Et₂O/EtOAc (4:1) to yield the title compound as a white-pink solid.

Step 3: (1R,5S,7S)-3-oxa-9-azabicyclo[3.3.1]nonan-7-yl 1H-indole-3-carboxylate, hydrogen chloride salt A suspension of (1R,5S,7S)-9-benzyl-3-oxa-9-azabicyclo[3.3.1]nonan-7-yl 1H-indole-3-carboxylate (2 g, 5.31 mmol) and palladium on carbon (200 mg, 1.879 mmol, 10 wt %) in EtOH (4.43 ml), THF (4.43 ml) and 3N HCl (4.43 ml) was stirred at RT under a hydrogen atmosphere (balloon) for 14 h. Then, the mixture was filtered through a pad of Celite and the filtrate was concentrated under reduced pressure to afford the title compound as a pink solid, which was used without further purification.

Step 4: (1R,5S,7S)-tert-butyl 7-((1H-indole-3-carbonyl)oxy)-3-oxa-9-azabicyclo[3.3.1]nonane-9-carboxylate Di-tert-butyl dicarbonate (1.275 g, 5.84 mmol) was added in one portion to a suspension of (1R,5S,7S)-3-oxa-9-azabicyclo[3.3.1]nonan-7-yl 1H-indole-3-carboxylate hydrochloride (1.714 g, 5.31 mmol) and triethylamine (1.628 ml, 11.68 mmol) in THF (26.6 ml) at RT. After 1 h, the mixture was partitioned between sat. NH₄Cl (aq) and ethyl acetate. The aqueous layer was extracted with ethyl acetate and combined organic layers were washed with brine, dried over anhydrous Na₂SO₄, filtered and concentrated under reduced pressure to afford the title compound as a pale-brown oil, which was used without further purification.

Reference 9

Synthesis of 1-(pyridin-2-yl)-1H-pyrrolo[2,3-b]pyridine-3-carboxylic acid

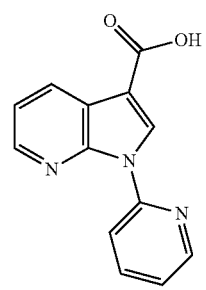 [SMILES: O=C(O)c1cn(-c2ccccn2)c2ncccc12]

Step 1: methyl 1-(pyridin-2-yl)-1H-pyrrolo[2,3-b]pyridine-3-carboxylate

Sodium hydride (22.70 mg, 0.568 mmol, 60% suspension in mineral oil) was added to a solution of methyl 1H-pyrrolo

[2,3-b]pyridine-3-carboxylate (100 mg, 0.568 mmol) in DMF (1419 μl) at RT. After 10 min, 2-fluoropyridine (48.8 μl, 0.568 mmol) was added to the mixture and the mixture was heated at 100° C. for 14 h. After being cooled to RT, the reaction mixture was directly purified by HPLC followed by neutralization (aq. NaHCO₃) to afford the title compound as a colorless film.

Step 2: 1-(pyridin-2-yl)-1H-pyrrolo[2,3-b]pyridine-3-carboxylic acid

Potassium hydroxide (11.30 mg, 0.201 mmol) was added to a solution of methyl 1-(pyridin-2-yl)-1H-pyrrolo[2,3-b]pyridine-3-carboxylate (10.2 mg, 0.040 mmol) in MeOH (67.1 μl) and water (67.1 μl) at RT. The mixture was heated at 90° C. for 2 h. The organic layer was extracted into ethyl acetate after acidifying the mixture with 0.5 N citric acid. The combined organic layers were washed with brine, dried over Na₂SO₄, filtered and concentrated under reduced pressure to afford the title compound as a white solid, which was used without further purification.

The following carboxylic acids were prepared by a similar procedure:
5-fluoro-1-(pyridin-2-yl)-1H-pyrrolo[2,3-b]pyridine-3-carboxylic acid and 1-(pyridin-2-yl)-1H-indazole-3-carboxylic acid.

Example 1

Synthesis of (1R,5S,7S)-3-oxa-9-azabicyclo[3.3.1]nonan-7-yl 1-(pyridin-3-yl)-1H-indole-3-carboxylate bis(2,2,2-trifluoroacetate)

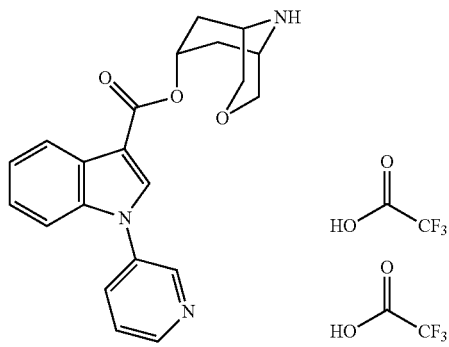

Step 1: (1R,5S,7S)-tert-Butyl 7-((1-(pyridin-3-yl)-1H-indole-3-carbonyl)oxy)-3-oxa-9-azabicyclo[3.3.1]nonane-9-carboxylate Copper(I) iodide (21.99 mg, 0.115 mmol) was added to a suspension of (1R,5S,7S)-tert-butyl 7-((1H-indole-3-carbonyl)oxy)-3-oxa-9-azabicyclo[3.3.1]nonane-9-carboxylate (163.6 mg, 0.423 mmol), 3-bromopyridine (37.1 μl, 0.385 mmol), trans-N,N'-dimethylcyclohexane-1,2-diamine (36.9 μl, 0.231 mmol) and potassium phosphate (172 mg, 0.808 mmol) in toluene (Volume: 770 μl) at RT. The mixture was heated at 110° C. for 14 h. The mixture was then concentrated and directly purified by column chromatography (SiO₂: EA/hex) to afford the title compound as a yellow foam.

Step 2 (1R,5S,7S)-3-Oxa-9-azabicyclo[3.3.1]nonan-7-yl 1-(pyridin-3-yl)-1H-indole-3-carboxylate bis(2,2,2-trifluoroacetate)

TFA (Volume: 356 μl, Ratio: 1.000) was added to a solution of (1R,5S,7S)-tert-butyl 7-((1-(pyridin-3-yl)-1H-indole-3-carbonyl)oxy)-3-oxa-9-azabicyclo[3.3.1]nonane-9-carboxylate (164.8 mg, 0.356 mmol) in DCM (Volume: 356 μl, Ratio: 1.000) at rt. After 15 min, the mixture was diluted with DMF, filtered and purified by HPLC to afford the title compound as a pale-yellow oil to afford the title compound as a yellow oil. MS (ESI, pos. ion) m/z: 364.2 (M+1).

The following compounds were prepared by a similar procedure, where Boc group was removed either with TFA or HCl: (1R,5S,7S)-3-oxa-9-azabicyclo[3.3.1]nonan-7-yl 1-(1-methyl-1H-pyrazol-4-yl)-1H-indole-3-carboxylate, 2,2,2-trifluoroacetic acid salt; (1R,5S,7S)-3-oxa-9-azabicyclo[3.3.1]nonan-7-yl 1-(1-methyl-1H-pyrazol-3-yl)-1H-indole-3-carboxylate, 2,2,2-trifluoroacetic acid salt; and (1R,5S,7S)-3-oxa-9-azabicyclo[3.3.1]nonan-7-yl 1-(1-methyl-1H-pyrazol-5-yl)-1H-indole-3-carboxylate, 2,2,2-trifluoroacetic acid salt.

Example 2

Synthesis of 1-(1-methyl-1H-pyrazol-3-yl)-N-((1R,5S,7S)-9-methyl-3-oxa-9-azabicyclo[3.3.1]nonan-7-yl)-1H-indole-3-carboxamide, 2,2,2-trifluoroacetic acid salt

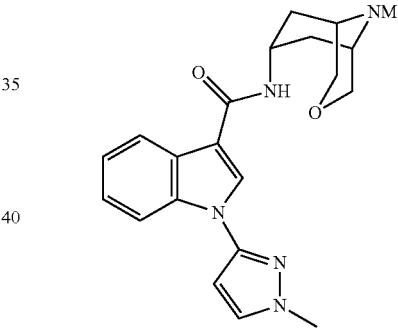

To a mixture of 1-(1-methyl-1H-pyrazol-3-yl)-1H-indole-3-carboxylic acid hydrochloride (25 mg, 0.090 mmol) in DMF (Volume: 900 μl) was added HATU (37.7 mg, 0.099 mmol) and N-ethyl-N-isopropylpropan-2-amine (79 μl, 0.450 mmol). After the reaction mixture was stirred at rt for 15 min, (1R,5S,7S)-9-methyl-3-oxa-9-azabicyclo[3.3.1]nonan-7-amine 2,2,2-trifluoroacetate (29.2 mg, 0.108 mmol) was added and stirring was continued for 2 h. HPLC purification gave the title compound as a white solid. MS (ESI, pos. ion) m/z: 380.25 (M+1)

The following compounds were prepared by a similar procedure, either with commercially available carboxylic acids or those synthesized according to reference compound procedures:
1-(1-methyl-1H-pyrazol-4-yl)-N-((1R,5S,7S)-9-methyl-3-oxa-9-azabicyclo[3.3.1]nonan-7-yl)-1H-indole-3-carboxamide, 1-(1-methyl-1H-pyrazol-5-yl)-N-((1R,5S,7S)-9-methyl-3-oxa-9-azabicyclo[3.3.1]nonan-7-yl)-1H-indole-3-carboxamide, 2,2,2-trifluoroacetic acid salt; and 1-(1-benzyl-1H-pyrazol-4-yl)-N-((1R,5S,7S)-9-methyl-3-oxa-9-azabicyclo[3.3.1]nonan-7-yl)-1H-indole-3-carboxamide 2,2,2-trifluoroacetate.

Example 3

Synthesis of (1R,5S,7S)-9-methyl-3-oxa-9-azabicyclo[3.3.1]nonan-7-yl 1-(1-(2-fluoroethyl)-1H-pyrazol-4-yl)-1H-indole-3-carboxylate, 2,2,2-trifluoroacetic acid salt

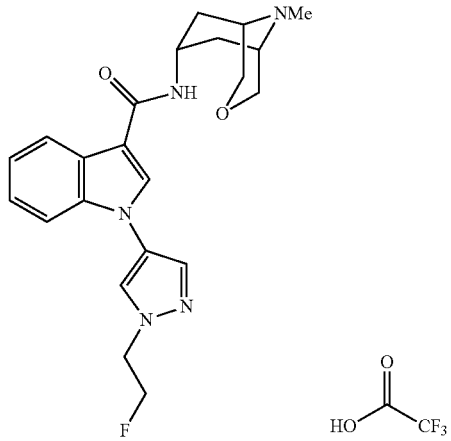 [SMILES: CN1C2COCC1CC(NC(=O)c1cn(-c3cnn(CCF)c3)c3ccccc13)C2 ; O=C(O)C(F)(F)F]

Step 1: 4-bromo-1-(2-fluoroethyl)-1H-pyrazole

Sodium hydride (24.22 mg, 0.606 mmol, 60% suspension in mineral oil) was added to a solution of 4-bromo-1H-pyrazole (89 mg, 0.606 mmol) in DMF (3028 µl) at RT. After 15 min, 1-bromo-2-fluoroethane (100 mg, 0.787 mmol) was added to the mixture. After 30 min, the mixture was diluted with DMF and purified by HPLC, followed by neutralization ($K_2CO_3$), to afford the title compound as a colorless oil.

Step 2: (1R,5S,7S)-9-methyl-3-oxa-9-azabicyclo[3.3.1]nonan-7-yl 1-(1-(2-fluoroethyl)-1H-pyrazol-4-yl)-1H-indole-3-carboxylate, 2,2,2-trifluoroacetic acid salt A mixture of (1R,5S,7S)-9-methyl-3-oxa-9-azabicyclo[3.3.1]nonan-7-yl 1H-indole-3-carboxylate (50 mg, 0.166 mmol), 4-bromo-1-(2-fluoroethyl)-1H-pyrazole (35.3 mg, 0.183 mmol), copper(I) iodide (9.51 mg, 0.050 mmol), N1,N1-dimethylethane-1,2-diamine (8.80 mg, 0.100 mmol) and potassium phosphate (74.2 mg, 0.350 mmol) in toluene (333 µl) was heated at 120° C. for 5 h. HPLC purification gave the title compound as a light-brown oil. MS (ESI, pos. ion) m/z: 413.30 (M+1).

Example 4

Synthesis of N-((1R,5S,7S)-9-methyl-3-oxa-9-azabicyclo[3.3.1]nonan-7-yl)-1-(1H-pyrazol-4-yl)-1H-indole-3-carboxamide, 2,2,2-trifluoroacetic acid salt

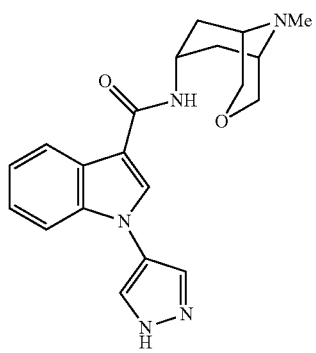 [SMILES: CN1C2COCC1CC(NC(=O)c1cn(-c3cn[nH]c3)c3ccccc13)C2]

A mixture of 1-(1-benzyl-1H-pyrazol-4-yl)-N-((1R,5S,7S)-9-methyl-3-oxa-9-azabicyclo[3.3.1]nonan-7-yl)-1H-indole-3-carboxamide 2,2,2-trifluoroacetate (85 mg, 0.149 mmol) and 10% Pd—C (120 mg) in MeOH (1.0 ml) was stirred at RT under $H_2$ for 2 days. Filtration and concentration afforded the title compound as a white solid. MS (ESI, pos. ion) m/z: 366.20 (M+1).

Example 5

Synthesis of 1-(1-methyl-1H-pyrazol-4-yl)-N-((1R,5S,7S)-9-methyl-3-oxa-9-azabicyclo[3.3.1]nonan-7-yl)-1H-indole-3-carboxamide, 2,2,2-trifluoroacetic acid salt

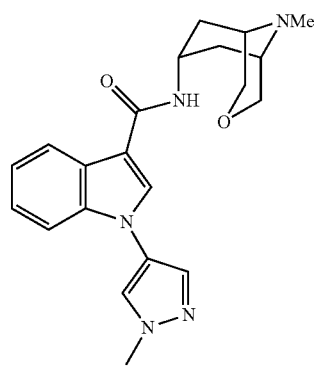 [SMILES: CN1C2COCC1CC(NC(=O)c1cn(-c3cnn(C)c3)c3ccccc13)C2]

Step 1: methyl 1-(1-methyl-1H-pyrazol-4-yl)-1H-indole-3-carboxylate, TFA

To a sealed tube was added copper(I) iodide (65.2 mg, 0.342 mmol), methyl 1H-indole-3-carboxylate (200 mg, 1.142 mmol) and potassium phosphate (509 mg, 2.397 mmol), then the reaction vessel was evacuated and purged with nitrogen (3x). Next, 4-bromo-1-methyl-1H-pyrazole (184 mg, 1.142 mmol) and (1R,2R)-N1,N2-dimethylcyclohexane-1,2-diamine (109 µl, 0.685 mmol) were added, followed by toluene (1142 µl). The reaction tube was evacuated and purged with nitrogen, then sealed and heated at 110° C. for 24 h. HPLC purification provided the title compound as a colorless oil.

Step 2: 1-(1-methyl-1H-pyrazol-4-yl)-1H-indole-3-carboxylic acid hydrochloride To a solution of methyl 1-(1-methyl-1H-pyrazol-4-yl)-1H-indole-3-carboxylate, TFA (3.5 mg, 9.48 µmol) in MeOH (95 µl) was added a solution of aq. KOH (33.2 µl, 0.066 mmol, 2 M). The reaction mixture was stirred at RT overnight, then acidified with 1N HCl. The solvent was evaporated under reduced pressure and the residue was dried under vacuum overnight. The title compound was used without further purification.

Step 3: 1-(1-methyl-1H-pyrazol-4-yl)-N-((1R,5S,7S)-9-methyl-3-oxa-9-azabicyclo[3.3.1]nonan-7-yl)-1H-indole-3-carboxamide, 2,2,2-trifluoroacetic acid salt To a mixture of 1-(1-methyl-1H-pyrazol-4-yl)-1H-indole-3-carboxylic acid hydrochloride (2.6 mg, 9.36 µmol) in DMF (187 μl) was added HATU (4.27 mg, 0.011 mmol) and DIPEA (8.18 μl, 0.047 mmol). After the reaction mixture was stirred at RT for 15 min, (1R,5S,7S)-9-methyl-3-oxa-9-azabicyclo[3.3.1]nonan-7-amine, TFA (3.04 mg, 0.011 mmol) was added and stirring was continued for 2 h. HPLC purification afforded the title compound as a white solid. MS (ESI, pos. ion) m/z: 380.30 (M+1).

Example 6

1-(1-(difluoromethyl)-1H-pyrazol-4-yl)-N-((1R,5S,7S)-9-methyl-3-oxa-9-azabicyclo[3.3.1]nonan-7-yl)-1H-indole-3-carboxamide, 2,2,2-trifluoroacetic acid salt

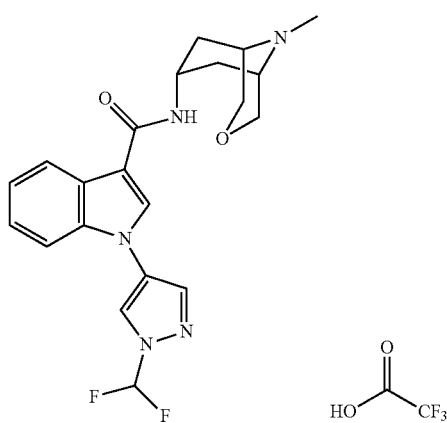 [SMILES: CN1C2COCC1CC(NC(=O)c1cn(-c3cnn(C(F)F)c3)c3ccccc13)C2 ; O=C(O)C(F)(F)F]

Step 1: 1-(1-(bromodifluoromethyl)-1H-pyrazol-4-yl)-N-((1R,5S,7S)-9-methyl-3-oxa-9-azabicyclo[3.3.1]nonan-7-yl)-1H-indole-3-carboxamide, 2,2,2-trifluoroacetic acid salt To a solution of N-((1R,5S,7S)-9-methyl-3-oxa-9-azabicyclo[3.3.1]nonan-7-yl)-1-(1H-pyrazol-4-yl)-1H-indole-3-carboxamide, 2,2,2-trifluoroacetic acid salt (30 mg, 0.063 mmol) in DMF (Volume: 626 μl) at 0° C. was added sodium hydride (7.51 mg, 0.188 mmol) and tetrabutylammonia bromide (0.202 mg, 0.626 μmol). After the resulting solution was stirred for 1 h, a solution of dibromodifluoromethane (5.78 μl, 0.063 mmol) in 0.1 mL DMF was added. The reaction mixture was gradually warmed up to RT over 2 h and stirred at RT for 2 h. HPLC purification afforded the title compound as a white solid.

Step 2: 1-(1-(difluoromethyl)-1H-pyrazol-4-yl)-N-((1R,5S,7S)-9-methyl-3-oxa-9-azabicyclo[3.3.1]nonan-7-yl)-1H-indole-3-carboxamide, 2,2,2-trifluoroacetic acid salt A solution of 1-(1-(bromodifluoromethyl)-1H-pyrazol-4-yl)-N-((1R,5S,7S)-9-methyl-3-oxa-9-azabicyclo[3.3.1]nonan-7-yl)-1H-indole-3-carboxamide, 2,2,2-trifluoroacetic acid salt (4 mg, 6.58 μmol) and TBAF (3.44 mg, 0.013 mmol) in sulfolane (Volume: 32.9 μl) was slowly heated to 170-180° C. HPLC purification afforded the title compound as a white solid film. MS (ESI, pos. ion) m/z: 416.30 (M+1).

Example 7

N-((1R,5S,7S)-3-oxa-9-azabicyclo[3.3.1]nonan-7-yl)-1-(1-methyl-1H-pyrazol-4-yl)-1H-indole-3-carboxamide, 2,2,2-trifluoroacetic acid salt

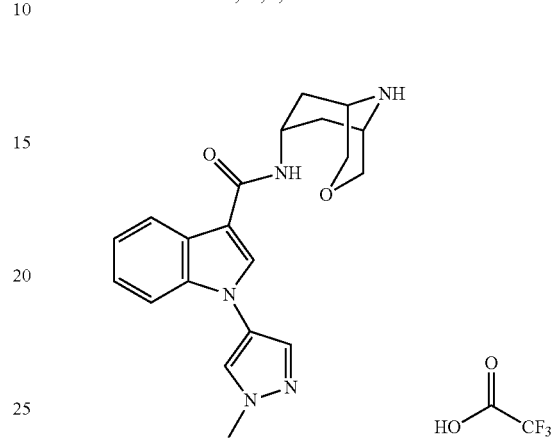

Step 1: tert-Butyl (1R,5S,7S)-7-(1-(1-methyl-1H-pyrazol-4-yl)-1H-indole-3-carboxamido)-3-oxa-9-azabicyclo[3.3.1]nonane-9-carboxylate To a solution of 1-(1-methyl-1H-pyrazol-4-yl)-1H-indole-3-carboxylic acid hydrochloride (25 mg, 0.090 mmol) and HATU (37.7 mg, 0.099 mmol) in DMF (Volume: 450 μl) was added N-ethyl-N-isopropylpropan-2-amine (62.9 μl, 0.360 mmol). After the reaction solution was stirred at RT for 15 min, (1R,5S,7S)-tert-butyl 7-amino-3-oxa-9-azabicyclo[3.3.1]nonane-9-carboxylate (24.00 mg, 0.099 mmol) was added. The stirring was continued for 1 h. HPLC purification followed by ISCO (0-20% MeOH in DCM) purification gave the title compound as a white solid.

Step 2: N-((1R,5S,7S)-3-oxa-9-azabicyclo[3.3.1]nonan-7-yl)-1-(1-methyl-1H-pyrazol-4-yl)-1H-indole-3-carboxamide, 2,2,2-trifluoroacetic acid salt A solution of tert-Butyl (1R,5S,7S)-7-(1-(1-methyl-1H-pyrazol-4-yl)-1H-indole-3-carboxamido)-3-oxa-9-azabicyclo[3.3.1]nonane-9-carboxylate (18.1 mg, 0.039 mmol) in TFA (Volume: 194 μl, Ratio: 1) and DCM (Volume: 194 μl, Ratio: 1) was stirred at RT for 1 h. Removal of the solvent gave the title compound as a white solid. MS (ESI, pos. ion) m/z: 366.25 (M+1).

The following compound was prepared by a similar procedure:

N-((1R,5S,7S)-3-oxa-9-azabicyclo[3.3.1]nonan-7-yl)-1-(pyridin-3-yl)-1H-indole-3-carboxamide.

Example 8

N-((1R,5S,7S)-9-ethyl-3-oxa-9-azabicyclo[3.3.1]nonan-7-yl)-1-(1-methyl-1H-pyrazol-4-yl)-1H-indole-3-carboxamide, 2,2,2-trifluoroacetic acid salt

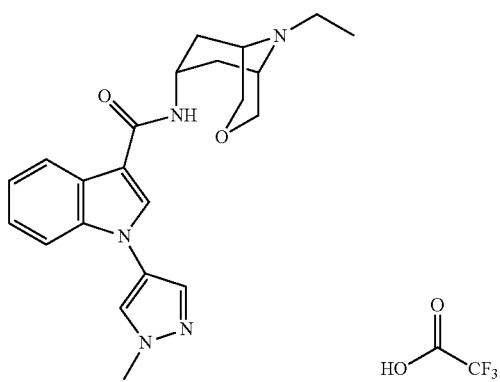 [SMILES: CCN1C2COCC1CC(NC(=O)c1cn(-c3cnn(C)c3)c3ccccc13)C2 ; O=C(O)C(F)(F)F]

A mixture of N-((1R,5S,7S)-3-oxa-9-azabicyclo[3.3.1]nonan-7-yl)-1-(1H-pyrazol-4-yl)-1H-indole-3-carboxamide, 2,2,2-trifluoroacetic acid salt (12 mg, 0.025 mmol), triethylamine (5.13 µl, 0.038 mmol), and acetaldehyde (2.120 µl, 0.038 mmol) in DCE (Volume: 250 µl) was stirred for 10 min at RT. Then, sodium triacetoxyhydroborate (10.61 mg, 0.050 mmol) was added at RT. The mixture was stirred for 16 h and quenched with a few drops of water. HPLC purification afforded the title compound as a white solid. MS (ESI, pos. ion) m/z: 394.35 (M+1).

Example 9

3-(3-(((1R,5S,7S)-9-methyl-3-oxa-9-azabicyclo[3.3.1]nonan-7-yl)carbamoyl)-1H-indol-1-yl)pyridine 1-oxide, 2,2,2-trifluoroacetic acid salt

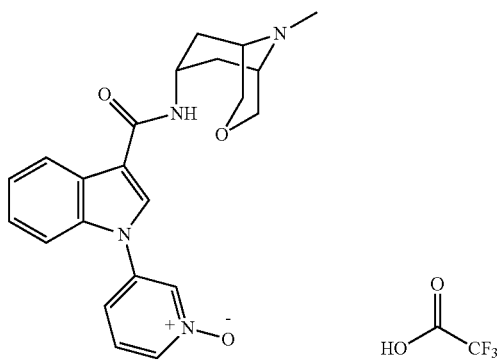

A mixture of N-((1R,5S,7S)-9-methyl-3-oxa-9-azabicyclo[3.3.1]nonan-7-yl)-1-(pyridin-3-yl)-1H-indole-3-carboxamide (20 mg, 0.053 mmol) and meta-chloroperoxybenzoic acid (10.08 mg, 0.058 mmol) in DCM (Volume: 0.8 ml) was stirred at RT for 2 h. HPLC purification gave the title compound as a white solid. MS (ESI, pos. ion) m/z: 393.30 (M+1).

BIOLOGICAL EXAMPLES

Biological Example 1

Inhibition of Ca Flux Activity of 5-HT3 In Vitro Assay

The 5-HT3 antagonist activity of the compounds of the invention was determined by measuring the ability of the compounds to inhibit the calcium flux activity of 3HT3a receptor expressed in HEK-293T cells. HEK-293T cells were transfected with the 5-HT3a expression construct using Xtreme Gene 9 (Roche) in 150 mm tissue culture treated plates and incubated for 24 hours at 37° C. Cells were then split and plated at a density of 60K cells/well in poly-lysine coated, black 96-well plates with clear bottoms (BD BioSciences) and incubated overnight at 37° C. Growth media was removed and cells loaded with 200 uL calcium indicator dye in HBSS containing 20 mM HEPES (Calcium 5 Assay kit, Molecular Devices) and incubated at 37° C. for 1 hour. While cells were incubating, the 10× antagonist and agonist/antagonist addition plates were made. For 10× antagonist plate: half log serial dilutions (final concentrations range from $10^{-7}$ through $10^{-10}$ with the bottom well a negative, no ligand control) were made from test compounds in DMSO at a 1000× concentration and then diluted to 10× in HBSS/20 mM HEPES. For addition plate: 5HT was diluted to 100× in HBSS/20 mM HEPES (final concentration in the assay-216 nM) and 15 uL was added to each well of the addition plate, 15 uL of 10× compound was also added to the addition plate, and finally 120 uL of HBSS/20 mM HEPES (for a total of 150 uL). Cells were then removed from the incubator and equilibrated to room temperature for 10 minutes, then 22.5 uL of 10× test compounds were added in triplicate to the plates and incubated at room temperature for 10 minutes (Tropisetron was used as a positive control in every assay). Test plate and addition plate were loaded into the FlexStation III (Molecular Devices), and using the fluidics, 22.5 uL compound additions were made (at t=~17 seconds), and fluorescence was measured for 90 seconds, reading every 2.2 seconds. Data sets were analyzed as max minus min using Software Max Pro (Molecular Devices). $IC_{50}$ curves were generated using non-linear regression in GraphPad Prism.

Approximate $IC_{50}$ value of a representative number of compounds of Formula (I) in this assay are provided in the Table 2 below.

TABLE 2

| Cpd. No. from Table I above | IC50 [nM] | Cpd. No. from Table I above | IC50 [nM] | Cpd. No. from Table I above | IC50 [nM] |
| --- | --- | --- | --- | --- | --- |
| 1 | 0.95 | 2 | 0.51 | 3 | 0.96 |
| 4 | 0.69 | 5 | 0.62 | 6 | 1.1 |
| 7 | 2.86 | 8 | 0.81 | 9 | 0.68 |
| 10 | 0.65 | 11 | 0.60 | 12 | 0.8825 |
| 13 | 0.72 | 14 | 1.34 | 15 | 0.662 |
| 16 | 2.5 | 17 | 0.75 | 18 | 2.013 |
| 19 | 3.68 | 20 | 1.5 | 21 | 1.10 |
| 22 | 0.65 | 23 | 1.01 | 25 | 1.39 |
| 26 | 1.20 | 27 | 1.44 | 28 | 2.04 |
| 29 | 0.462 | 30 | 0.745 | 31 | >1000 |
| 32 | 1.36 | | | | |

In addition, in a head-to-head comparative study Compound 15 of Table 1, Example 5, had an IC50 of 3.48 in this assay, while the compound of example Reference 7 above had an IC50 in this assay of 89.1 nM.

Biological Example 2

Rodent Novel Object Recognition (NOR) Assay in Phencyclidine-induced Cognitive Deficits Modeling Schizophrenia The aim of this study is to investigate the ability of the compounds of the invention to improve subchronic PCP-induced impairment in cognition memory using the NOR task in the rat, a paradigm of relevance to cognition in schizophrenia. Adult male Sprague-Dawley rats (250-350 g; Harlan, USA) are used for the experiments. Animal are acclimated to the facility for 7 days prior to experimentation. Seven groups of 14 animals per group are used for the experiment. One group of animals receive vehicle (0.9% saline twice daily) and the remaining six groups receive PCP (2.5 mg/kg, s.c. twice daily) for 7 days, followed by 5-days drug free. On the test day, the animals are allowed to acclimate to the testing room for 30 min prior to initiation of experiments. Experiments are carried out in a white plexi-glass chamber, designated as the experimental arena. The arena is placed in a dark experimental room that is illuminated by a halogen lamp, providing a dim light to the arena.

Animals are placed in the arena for a 5 minute period to freely explore the test chamber in the absence of objects (habituation). Animals are then returned to their home cage immediately upon completion of habituation for a 120 min period. The test compound (0.1, 1, 10 mg/kg s.c.), or vehicle (veh, saline) is administered 120 min prior to T1 and galantamine (5 mg/kg, i.p.) is administered 30 min prior to T1. Animals are returned to the arena which contained two identical objects (plastic balls) placed at one end of the arena (acquisition, T1), and allowed to explore for a 5 min period. The time spent exploring the two objects is recorded. Animals are once again returned to the home cage for a period of 120 min (ITI).

ITI is followed by the retention phase (T2) where one of the objects presented in the first trial is replaced by a novel object and animals are allowed to explore for an additional 5 min period. Again, the time spent exploring the two objects is recorded.

For the retention phase, the differences between the time spent exploring the familiar object and the novel object are examined. All sessions are recorded and scored blindly for the time exploring objects. Exploration is defined as touching the object or directing nose towards object at a distance less that 2 cm. A minimal exploration criterion is used such that only animals with exploration time of greater than 5 seconds per object are included.

Comparisons of all treatment groups are conducted using a one-way ANOVA followed by a Bonferroni's post hoc test for multiple comparisons.

Biological Example 3

Nicotinic α-7 Receptor Binding Assay

The evaluation of binding at the nicotinic α-7 receptor was carried out at Eurofins Pharma Services. Compound 15 of Table 1, Example 5, had an IC50 in this assay of >10 μM while the compound of Reference 7 above had an IC50 in this assay of 1.66 μM.

Formulation Examples

The following are representative pharmaceutical formulations containing a compound of Formula (I).

Tablet Formulation

The following ingredients are mixed intimately and pressed into single scored tablets.

| Ingredient | Quantity per tablet |
| --- | --- |
| compound of this invention | 0.5-150 mg |
| cornstarch | 50 mg |
| croscarmellose sodium | 25 mg |
| lactose | 120 mg |
| magnesium stearate | 5 mg |

Capsule Formulation

The following ingredients are mixed intimately and loaded into a hard-shell gelatin capsule.

| Ingredient | Quantity per capsule |
| --- | --- |
| compound of this invention | 0.5-150 mg |
| lactose spray dried | 148 mg |
| magnesium stearate | 2 mg |

Injectable Formulation

Compound of the invention (e.g., compound 1) in 2% HPMC, 1% Tween 80 in DI water, pH 2.2 with MSA, q.s. to at least 20 mg/mL.

What is claimed is:

1. A compound of Formula (I):

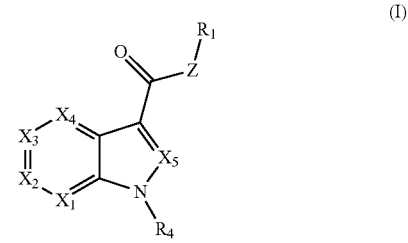

or a pharmaceutically acceptable salt thereof or N-oxide thereof, wherein:

Z is O or $NR_a$, wherein is hydrogen or $C_{1-6}$ alkyl;

$R_1$ is a ring of the formula (a)-(h) below:

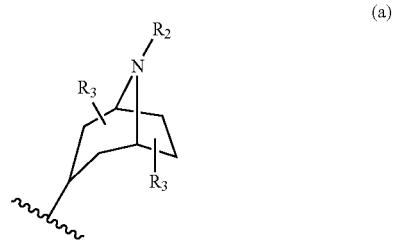

-continued

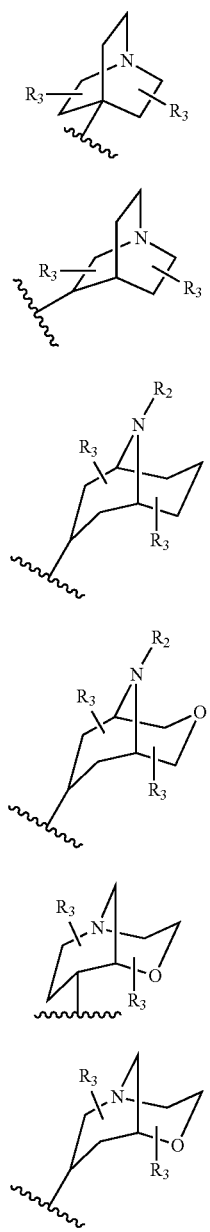

(b)

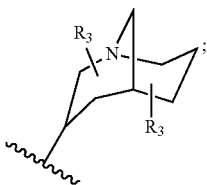

(c)

R₂ is hydrogen, C₁₋₆ alkyl, or C₁₋₆ haloalkyl;
each R₃ is independently hydrogen, C₁₋₆ alkyl, C₁₋₆ alkoxy, C₁₋₆ haloalkoxy, or halo, and can be present on any carbon atom in the rings;
R₄ is pyridinyl or pyrazolyl, each optionally substituted with one or two substituents independently selected from C₁₋₆ alkyl, C₁₋₆ haloalkyl, C₁₋₆ haloalkoxy, C₁₋₆ alkoxy, cyano, and halo;
X₁, X₂, X₃, and X₄ are each CR₅;
each R₅ is independently hydrogen, C₁₋₆ alkyl, halo, hydroxy, or cyano, provided that at least one of R₅ is hydrogen; and
X₅ is N.

2. The compound or pharmaceutically acceptable salt of claim 1, wherein R₁ is a ring of formula (a) or (d).

3. The compound or pharmaceutically acceptable salt of claim 1, wherein R₁ is a ring of formula (e), (f), or (g).

4. The compound or pharmaceutically acceptable salt of claim 1, wherein R₁ is a ring of formula (e).

5. The compound or pharmaceutically acceptable salt of claim 1, wherein each R₃ is hydrogen.

6. The compound or pharmaceutically acceptable salt of claim 1, wherein R₂ is hydrogen and each R₃ is hydrogen.

7. The compound or pharmaceutically acceptable salt of claim 1, wherein each R₃ is independently hydrogen or methyl and R₂ is C₁₋₆ alkyl.

8. The compound or pharmaceutically acceptable salt of claim 1, wherein R₂ is methyl and each R₃ is hydrogen.

9. The compound or pharmaceutically acceptable salt of claim 1, wherein each R₅ is hydrogen.

10. The compound of claim 1 which is
N-((1R,5S,7S)-9-methyl-3-oxa-9-azabicyclo[3.3.1]nonan-7-yl)-1-(pyridin-2-yl)-1H-indazole-3-carboxamide or a pharmaceutically acceptable salt of each above mentioned compound.

11. A pharmaceutical composition comprising a compound as defined in claim 1 and a pharmaceutically acceptable excipient.

* * * * *